(12) United States Patent
Rotello et al.

(10) Patent No.: US 8,003,404 B2
(45) Date of Patent: Aug. 23, 2011

(54) METHODS AND COMPOSITIONS FOR PATHOGEN DETECTION USING NANOPARTICLE-FLUORESCENT POLYMER COMPLEXES

(75) Inventors: Vincent Rotello, Belchertown, MA (US); Uwe Bunz, Atlanta, GA (US); Ronnie Phillips, Atlanta, GA (US); Oscar Miranda, Amherst, MA (US); Chang-Cheng You, Waltham, MA (US)

(73) Assignee: University of Massachusetts, Boston, MA (US)

( * ) Notice: Subject to any disclaimer, the term of this patent is extended or adjusted under 35 U.S.C. 154(b) by 239 days.

(21) Appl. No.: 12/313,137

(22) Filed: Nov. 17, 2008

(65) Prior Publication Data

US 2010/0021960 A1    Jan. 28, 2010

Related U.S. Application Data

(60) Provisional application No. 61/004,471, filed on Nov. 28, 2007.

(51) Int. Cl.
*G01N 21/76* (2006.01)
(52) U.S. Cl. ......... 436/172; 436/164; 436/169; 436/171
(58) Field of Classification Search .................. None
See application file for complete search history.

(56) References Cited

OTHER PUBLICATIONS

You et al. "Detection and identification of proteins using nanoparticle-fluorescent polymer 'chemical nose' sensors", Nature nanotechnology, May 2007, v. 2, pp. 318-323.*
Kaufman et al. "Green fluorescent protein (GFP) as a vital marker for pathogenic development of the dermatophyte Trichophyton mentagrophytes", Microbiology, 2004, v. 150, pp. 2785-2790.*
Kim, I-B; Phillips, R; Bunz, UHF. Carboxylate Group Side-Chain Density Modulates the pH-Dependent Optical Properties of PPEs. Macromolecules 2007 40 (15), 5290-5293; published on Web Jun. 21, 2007.
Fialkowski, M; Bishop, KJM; Chubukow, VA; Campbell CJ; Grzbowski, BA. Architecture and Evolution of Organic Chemistry. Angew. Chem. Int. Ed. 2005, 44, pp. 7263-7269.
Bishop KJM; Klajn, R; Grzbowski, BA. The Core and Most Useful Molecules in Organic Chemistry. Angew. Chem. Int. Ed. 2006, 45, pp. 5348-5354.
De, M; Rana, S; Akpinar, H; Miranda, OR; Arvizo, RR; Bunz, UHF; Rotello, VM. Sensing of Proteins in human serum using conjugates of nanoparticles and green fluorescent protein. Nature Chemistry, vol. 1, Sep. 2009, pp. 461-465.
Bajaj, A; Miranda, OR; Kim, I-B; Phillips, RL; Jerry, DJ; Bunz, UHF. Detection and differentiation of normal, cancerous, and metastatic cells using nanoparticle-polymer sensor arrays. PNAS, Jul. 7, 2009, vol. 106, No. 27, pp. 10912-10916.

* cited by examiner

*Primary Examiner* — Yelena G Gakh
(74) *Attorney, Agent, or Firm* — Milstein Zhang & Wu LLC

(57) ABSTRACT

Compositions, methods and related apparatus, as can be used for selective pathogen detection and identification.

21 Claims, 6 Drawing Sheets

Figures 3B-C
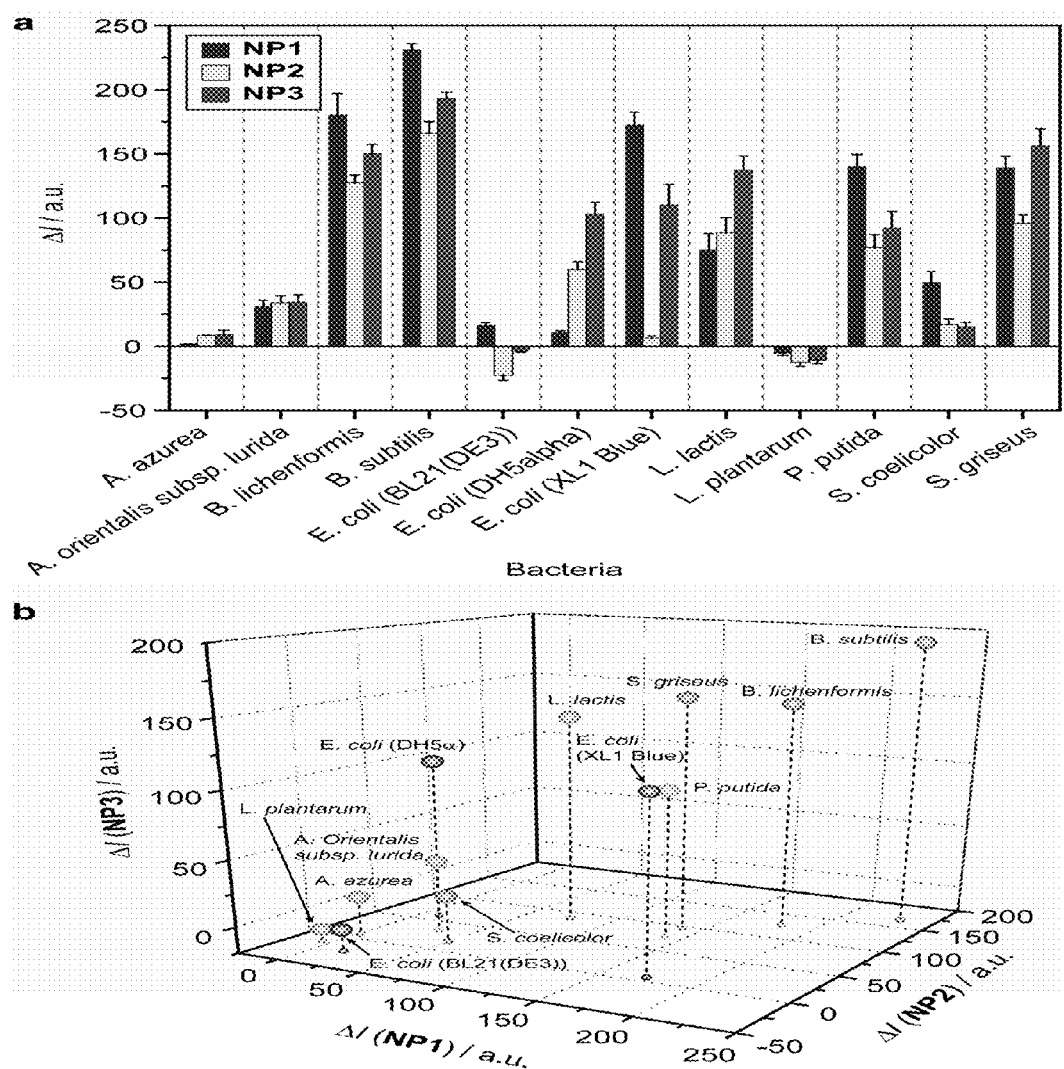

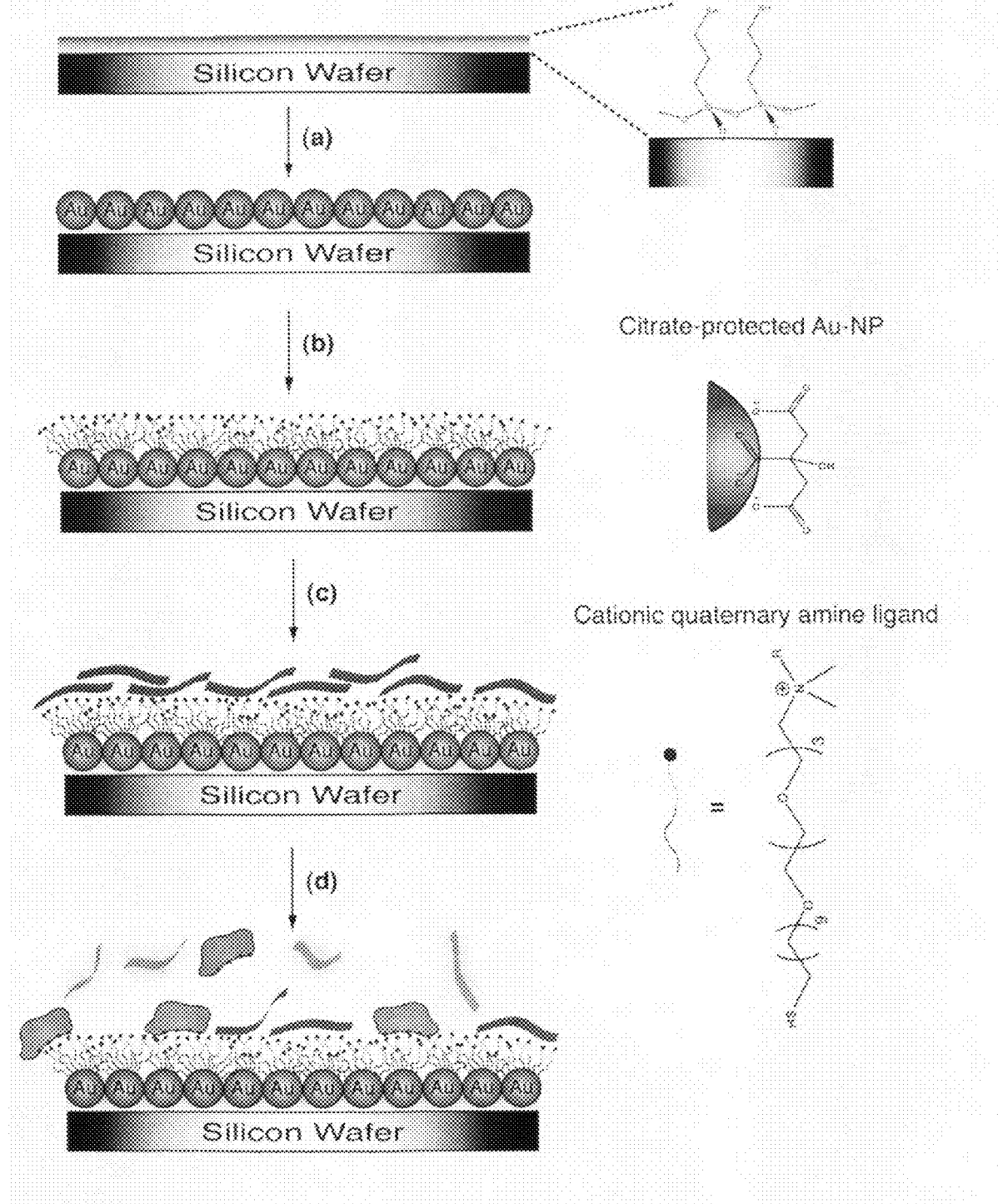

METHODS AND COMPOSITIONS FOR PATHOGEN DETECTION USING NANOPARTICLE-FLUORESCENT POLYMER COMPLEXES

This application claims priority benefit from application Ser. No. 61/004,471 filed Nov. 28, 2007, the entirety of which is incorporated herein by reference.

The United States Government has certain rights to this invention pursuant to Grant Nos. GM077173 and DMI-0531171 from the National Institutes of Health and the National Science Foundation, respectively, to the University of Massachusetts, and Grant No. DE-FG02-04ER46141 from the Department of Energy to the Georgia Institute of Technology.

BACKGROUND OF THE INVENTION

Fast and efficient identification of pathogens in water, blood serum and other biological fluids is an important yet unsolved issue in medical, forensic and environmental sciences. Conventional plating and culturing are generally used to identify causative bacterial pathogens in clinical environments. While more technologically advanced systems have been developed for specific microorganisms, these methods are generally complex or require sophisticated instrumentation. Plating and culturing is highly accurate, but it is time consuming and requires at least 24 h. Point-of-care treatment decisions are therefore made without having access to crucial microbiological information, often leading to the prescription of a sub-optimal antibiotic. A specific example is the treatment of keflex- or methicillin-resistant *S. aureus* strains (MRSA) in community-acquired infections that require prompt treatment with either sulfa drugs or vancomycin. Researchers investigated >9000 cases of clinically reported bacterial infections and found that 85-90% were due to only seven pathogens with *S. aureus* and *E. coli* being responsible for half of all infections. (B. S. Reisner, G. L. Woods, *J. Clin. Microbiol.* 1999, 37, 2024-2026.) A simple, and rapid test that could discern the clinically most prevalent pathogens (e.g., bacterial, viral, fungal and others) would be of great value, allowing effective therapeutics against causative pathogens to be administered during the initial point-of-care visit in >85% of all cases. This capability would not only increase the efficacy of therapy, but would also reduce the occurrence of drug-resistant bacteria arising from inefficient antibiotics.

Likewise, the detection of bacteria and other pathogens plays a crucial role in environmental and food safety. For example, *E. coli* O157:H7 is a world-wide cause of foodborne illness which is responsible for more than 2000 hospitalizations and 60 deaths directly related to the corresponding bacterial infection each year in the United States, while the outbreak in Japan in 1996 resulted in 10000 infections and 11 deaths. (P. D. Frenzen, A. Drake, F. J. Angulo, *J. Food Prot.* 2005, 68, 2623-2630; M. D. Disney, J. Zheng, T. M. Swager, P. H. Seeberger, *J. Am. Chem. Soc.* 2004, 126, 13343-13346.) It has been demonstrated that the major outbreaks are associated with the contamination of unpasteurized juice, vegetables, and water, etc. (P. S. Mead, L. Slutsker, V. Dietz, L. F. McCaig, J. S. Bresee, C. Shapiro, P. M. Griffin, R. V. Tauxe, *Emerg. Infect. Dis.* 1999, 5, 607-625.) However, testing food for contamination before consumption is often absent due to the complex and/or lengthy analysis protocols.

SUMMARY OF THE INVENTION

In light of the foregoing, it is an object of the present invention to provide one or more pathogen detection methods and/or apparatus used therewith, thereby overcoming various deficiencies and shortcomings of the prior art, including those outlined above. It will be understood by those skilled in the art that one or more aspects of this invention can meet certain objectives, while one or more aspects can meet certain other objectives. Each objective may not apply equally, in all its respects, to every aspect of this invention. As such, the following objects can be viewed in the alternative with respect to any one aspect of this invention.

It can be an object of the present invention to provide, in comparison with sensor systems of the prior art, an approach to pathogen detection and/or identification which is relatively inexpensive, easily prepared and with data quickly processed and analyzed.

It can be another object of the present invention to provide one or more methods for pathogen detection, to quickly distinguish between both species and strains of pathogens including but not limited to bacteria, viruses, fungi, toxins and other biohazards without resort to marker systems of the prior art.

It can be another object of the present invention, alone or in conjunction with one or more of the preceding objectives, to provide an apparatus and/or kit for ready use in the detection and/or identification of unknown bacteria or other pathogens.

Other objects, features, benefits and advantages of the present invention will be apparent from this summary and the following descriptions of certain embodiments, and will be readily apparent to those skilled in the art having knowledge of various fluorescence-based detection methods. Such objects, features, benefits and advantages will be apparent from the above as taken into conjunction with the accompanying examples, data, figures and all reasonable inferences to be drawn therefrom.

In part, the present invention can be directed to a method of detecting the presence of a bacterium or another pathogen analyte. Such a method can comprise providing a non-covalent sensor complex comprising an ionic or otherwise functionalized (e.g., cationic) metal, metallic, semiconductor, metal oxide or other particle component and a polymer or biopolymer fluorophore component whether ionic, otherwise functionalized, or chemically complementary (e.g., anionic) to the particle component, such a complex having an initial, background or reference fluorescence; irradiating such a sensor complex; and monitoring an affect and/or change in fluorescence, such monitoring as can indicate no change, no analyte presence and/or a change not associated with an analyte of interest, and any such change as can be indicative of the presence of at least one pathogen analyte. In certain embodiments, such a particle component can comprise a hydrophilic moiety. In certain other embodiments, such a component can comprise a hydrophobic moiety. Regardless, ionic (e.g., cationic) character can be provided with a quaternary ammonium or other charged group. The compositional identity and/or dimension of such a particle component is limited only by pathogen surface interaction. Likewise, the composition of any such fluorophore component is limited only by complementary chemistry (e.g., anionic) with a particle component, measurable fluorescence and/or change thereof responsive to pathogen contact or interaction.

Regardless, in certain other embodiments, such a method can comprise a plurality of sensor complexes, each such complex as can provide a change in fluorescence responsive to the presence of a pathogen. As illustrated below, such complexes can be varied by fluorophore, particle and/or linker component, such variations as would be known to those skilled in the art made aware of this invention. Pathogen interaction can provide a fluorescence pattern indicative of the presence of a particular pathogen (e.g., bacteria) species and/or strain.

In part, the present invention can also be directed to a method of using fluorescent polymer, biopolymer or fluorogenic biopolymer displacement to detect and/or identify pathogen(s). Such a method can comprise providing a sensor complex of the sort described above, irradiated for a time and/or at a wavelength at least partially sufficient for initial fluorescence; (e.g., background fluorescence as can be due to quenching by a particle component) contacting such a complex with a pathogen species and/or strain, such contact and/or pathogen in an amount at least partially sufficient to affect fluorescence (e.g., the intensity or wavelength thereof); and monitoring the change in fluorescence upon such contact. The sensor complex employed with such a method can comprise one of those discussed above or illustrated elsewhere herein, alone or in combination with one or more other complexes as can be present. Regardless, such a complex can be irradiated at a wavelength at least partially sufficient for electronic excitement and/or fluorescence thereof. Likewise, as discussed above and illustrated elsewhere herein, contact with such a pathogen can be for a time and/or at a concentration at least partially sufficient to interact with the particle (e.g., without limitation metal, metallic, precious metal, metal oxide, sulfide or selenide and/or semiconductor) component of such a complex and/or to affect fluorescence of the fluorophore component. Such a bacterial or other pathogen species/strain can be present in the context of an unknown sample, the identity of which is limited by competitive and/or preferential interaction with such a particle component, as compared to particle component-fluorophore interaction. Alternatively, a pathogen can interact with a polymer component to displace the particle and alter complex fluorescence. Such a pathogen can be present in the context of an unknown sample or mixture, the identity of which is limited by competitive and/or preferential interaction with such a particle or polymer component, as compared to particle-fluorophore interaction. In certain embodiments, the presence of such a pathogen and preferential interaction can be observed to enhance fluorescent excited state, as can be indicated by a change in wavelength or intensity of fluorescence.

In part, the present invention can also be directed to a method detecting the presence of and/or identifying one or more unknown pathogen species and/or strains. Such a method can comprise providing reference spectral data comprising change in fluorescence for interaction of a sensor complex, of the sort described above, with a plurality of reference pathogen species/strains; comparing such reference data with change in fluorescence for interaction of such a sensor complex with unknown pathogens; and identifying the pathogen(s) on the basis of such a comparison. In certain embodiments, such reference data can comprise fluorescence changes from interaction of a plurality of such complexes with reference pathogen(s). As described above, such complexes can be varied by fluorophore component (e.g., π-conjugation and substitution) and/or fluorescence thereof. Without limitation as to number of sensor complexes employed comprising the reference data, pathogen identification can be made by direct spectral comparison. Use of a plurality of sensor complexes can provide a pattern of fluorescence changes, each such pattern as can be indicative of the presence of a particular pathogen species and/or strain. Alternatively, comparison can be made using one or more discriminate analysis techniques, as described below.

Alone or in conjunction with discriminate analysis, the present invention can also be directed to an apparatus for detection and/or identification of unknown pathogens. Without limitation as to physical embodiment or configuration, such a sensor apparatus can comprise a matrix comprising an array of a plurality of sensor complexes of the sort described herein. As illustrated below, such complexes can be chosen to provide differential changes in fluorescence, each such change responsive to a wide range of pathogen species and/or strains. Fluorescence change upon pathogen interaction and comparison with reference spectral data, as described above, can be used for discriminate pathogen identification.

Likewise, alone or in conjunction with one or more of the methodologies described herein, the present invention can also be directed to a kit for detection and/or identification of a bacteria or other pathogen in an analyte sample. Such a kit can comprise one or more nanoparticles with a coating component on or coupled thereto, such a coating component as can compromise charged or otherwise interactive terminal groups and one or more fluorophore components, each as described above or as would otherwise be understood by those skilled in the art made aware of this invention, for non-covalent bonding of one to another. Such a kit can optionally comprise a fluid medium conducive for pathogen interaction and/or fluorescence. Regardless, such a kit can also comprise a solid matrix component as can be employed with a plurality of such non-covalent sensor complexes and/or unknown pathogen samples.

Without limitation as to methodology, apparatus, kit or application context, the present invention can be directed to a nano-dimensioned particulate comprising a core component and a coating component on or coupled thereto, such a coating component as can comprise charged or otherwise interactive terminal groups. In certain embodiments, such a core component can, without limitation, comprise a metal, a metal oxide and/or a semiconductor material. Notwithstanding core identity, such a coating component can comprise ligands bearing a hydrophilic moiety or a hydrophobic moiety, the latter as can be selected from alkyl, oxa-substituted alkyl and/or poly(alkylene oxide) moieties. Regardless, such moieties can bridge such a terminal group, including but not limited to quaternary ammonium, and a coupling group including but not limited to sulfide. The coating component can also comprise polyelectrolytes including but not limited to polylysine, polyallylamine, polyethyleneimine, and their crosslinked entities. Such coatings and/or core components can be selected from those described more fully herein or as would be understood by those skilled in the art made aware of this invention, such selections and/or combinations limited only by protein interaction of the sort described herein.

Likewise, without limitation as to methodology, apparatus, kit or conjugation with one or more of the aforementioned particulates, this invention can be directed to a fluorogenic polymer of a formula

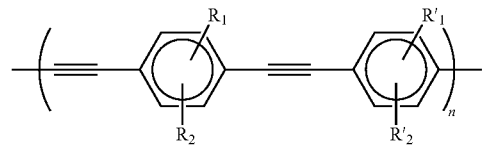

wherein $R_1$ and $R_2$ can be moieties independently selected from H, alkyl, oxa-substituted alkyl moieties and/or a moiety sterically configured to at least partially suppress non-specific polymer-pathogen interactions, providing at least one of $R_1$ and $R_2$ as such a steric configuration; and $R'_1$ and $R'_2$ can be moieties independently selected from charged moiety and counter ion pairs, such a selection at least partially sufficient for non-covalent interaction of such a polymer component with a particulate of the sort discussed above; and n can be an integer greater than 1 and corresponding to a number of repeating units as can be selected for desired π-conjugation, polymer fluorescence and/or quantum yield, such a component as can be terminated as described herein or as would be understood by those skilled in the art, depending upon reagent and/or reaction conditions. Without limitation, in certain embodiments, $R_1$ and $R_2$ can be independently selected from linear and branched oxa-substituted alkyl (e.g., poly(alkylene oxide)) moieties and $R'_1$ and $R'_2$ can independently comprise carboxylate and/or sulfate groups and corresponding alkali metal counter ions.

Alternatively, without limitation as to methodology, apparatus, kit or conjugation with one or more of the aforementioned particulates, this invention can be directed to a fluorogenic polymer of a formula

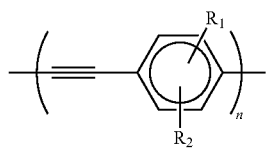

wherein $R_1$ and $R_2$ can be moieties independently selected from H and interactive moieties including but not limited to charged moiety and counter ion pairs, such a selection at least partially sufficient for non-covalent interaction of such a polymer component with a particulate of the sort discussed above; and n can be an integer greater than 1 and corresponding to a number of repeating units as can be selected for desired π-conjugation, polymer fluorescence and/or quantum yield, such a component as can be terminated as described herein or as would be understood by those skilled in the art, depending upon reagent and/or reaction conditions. Without limitation, in certain embodiments, $R_1$ and $R_2$ independently comprise carboxylate and/or sulfate groups and corresponding alkali metal counter ions. Without limitation, various such fluorogenic polymers are described in a co-pending application, entitled "Methods and Compositions for Protein Detection Using Fluorescent Polymer Sensors," filed contemporaneously herewith, the entirety of which is incorporated herein by reference.

As illustrated elsewhere herein, other fluorogenic polymers and/or biopolymers can also be used in conjunction with various particle components, apparatus and/or methods of this invention, such a polymer limited only by measurable fluorescence and/or change thereof responsive to pathogen contact or interaction. One non-limiting polymer can be green fluorescent protein, as described elsewhere herein and/or in the aforementioned incorporated reference. Various other polymers/biopolymers useful in the present context would be understood by those skilled in the art made aware of this invention.

BRIEF DESCRIPTION OF THE DRAWINGS

FIGS. 3B-C. Fluorescence response patterns of nanoparticle-polymer constructs in the presence of various bacteria ($OD_{600}$=0.05). B) Histograms of fluorescence intensity changes. Each value is an average of six parallel measurements and the error bars are shown. C) Three-dimensional representation of the fluorescence intensity changes against the three nanoparticle-polymer constructs.

FIG. 5. Schematic representation of an apparatus comprising a non-limiting nanoparticle and fabrication thereof.

DETAILED DESCRIPTION OF CERTAIN EMBODIMENTS

Figure 1:
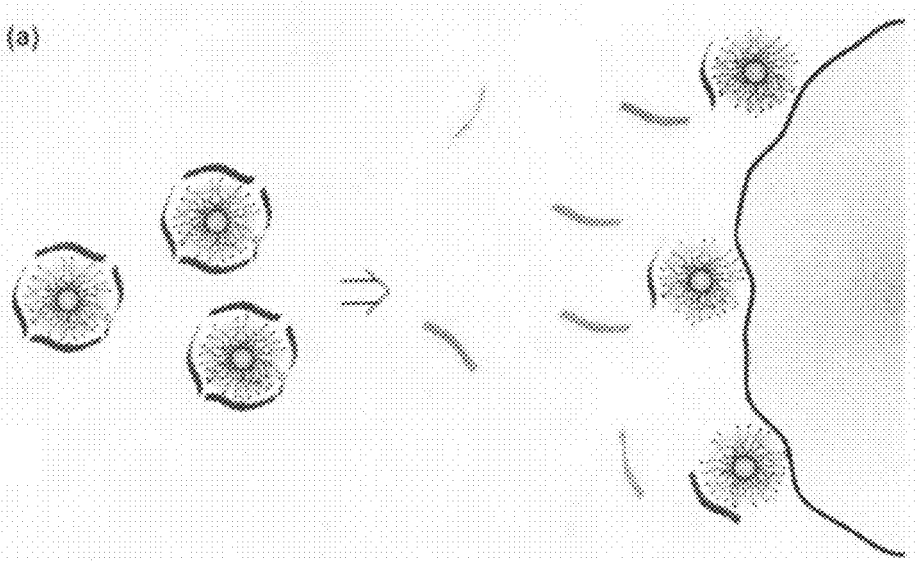
FIGS. 1A-B. Design of the nanoparticle-conjugated polymer sensor array. A) Schematic representation of the displacement of anionic conjugated polymers from cationic nanoparticles by negatively charged bacterial surfaces. B) Schematic illustration of fluorescence pattern generation on a microplate. In case of release from the nanoparticle, the initially quenched π-conjugated polymers regain their fluorescence. The fluorescence response is dependent upon the level of displacement determined by the relative binding strength of polymer-nanoparticle and bacteria-nanoparticle interactions. By modulating such interactions, the sensor array may generate distinct response patterns against different bacteria. In the diagram, codes A-G on the microplate represent bacteria of different types while codes 1-4 denote constructs built up from the functional nanoparticles.
Figure 1:
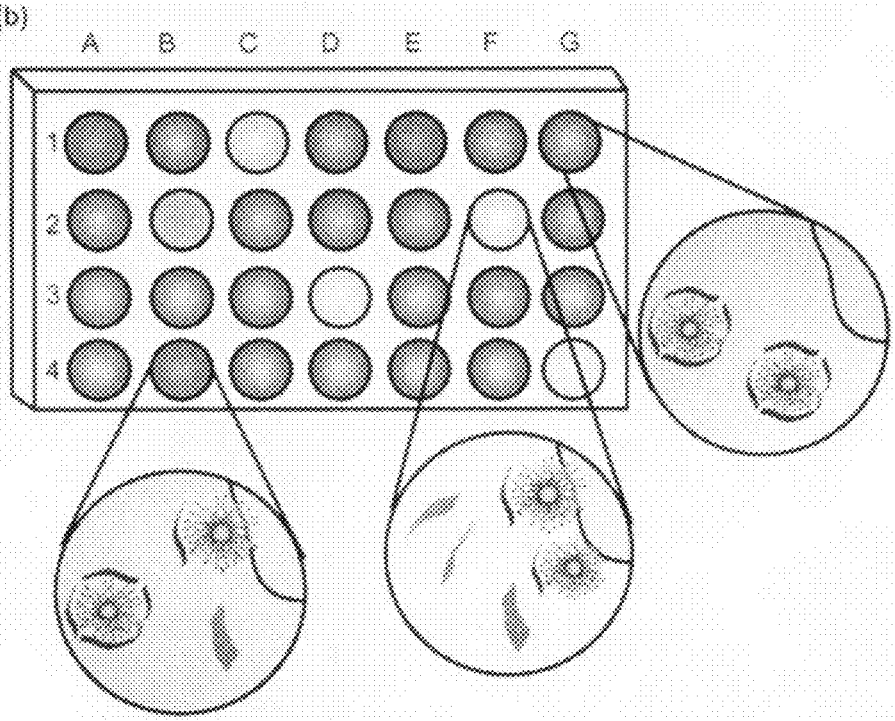

To address the issue of rapid identification of bacteria, this invention provides a protocol for bacterial sensing using an array of gold nanoparticle-conjugated polymer constructs. This sensing protocol adopts the concept of the 'chemical nose', where a series of analyte receptors are combined to differentiate targets according to their unique response diagrams. As shown in FIG. 1, an anionic conjugated polymer is initially associated with cationic gold nanoparticles to afford fluorescence-quenched complexes. In the presence of bacteria, a negatively-charged bacterial surface can competitively interact with the nanoparticles to release the polymer, restoring fluorescence. Without limitation to any one theory or mode of operation, nanoparticles feature a size that seem to enable recognition by extended patches of a hydrophobic or otherwise functionalized microorganism surface. For example, poly(L-lysine)-coated gold nanoparticles have been subjected to self-assembly with live bacteria through complementary electrostatic interactions. The polymer serves to transduce the binding event; the π-conjugated polymer used in this study provides both multivalency and the molecular wire effect to facilitate efficient signal generation in the sensing process. As functional "patches" (e.g. the charged residues and hydrophobic "hot spots") are prevalent on cell and microbial exteriors, this strategy has potential applications in the identification of a wide variety of cells, microbes, and viruses.

Figure 2:
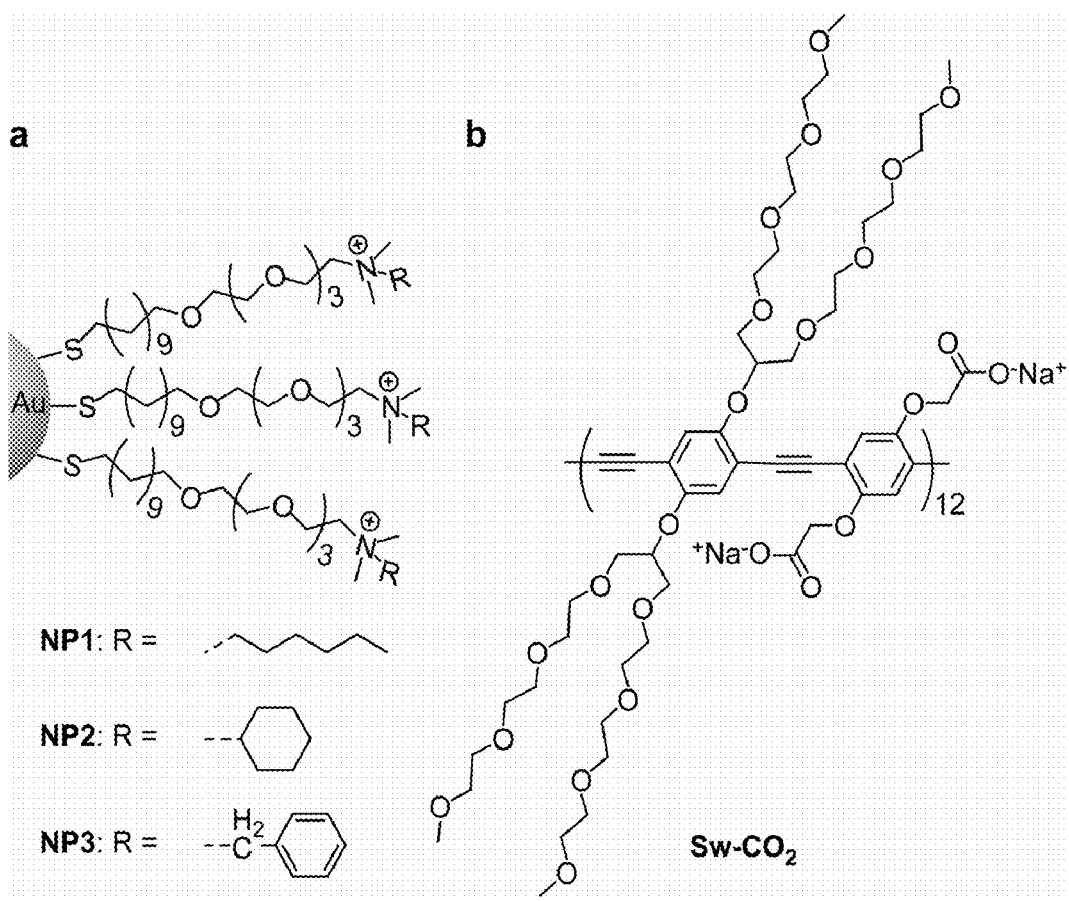
FIGS. 2A-B. Receptor and transducer components of the bacterial sensors. a) Structural representation of three cationic gold nanoparticles (NP1-NP3) with various hydrophobic tails. b) Chemical structure of the conjugated polymer (Sw-$CO_2$) featuring a branched oligo(ethylene glycol) side chain to suppress non-specific polymer-microorganism interactions.
Figure 3A:
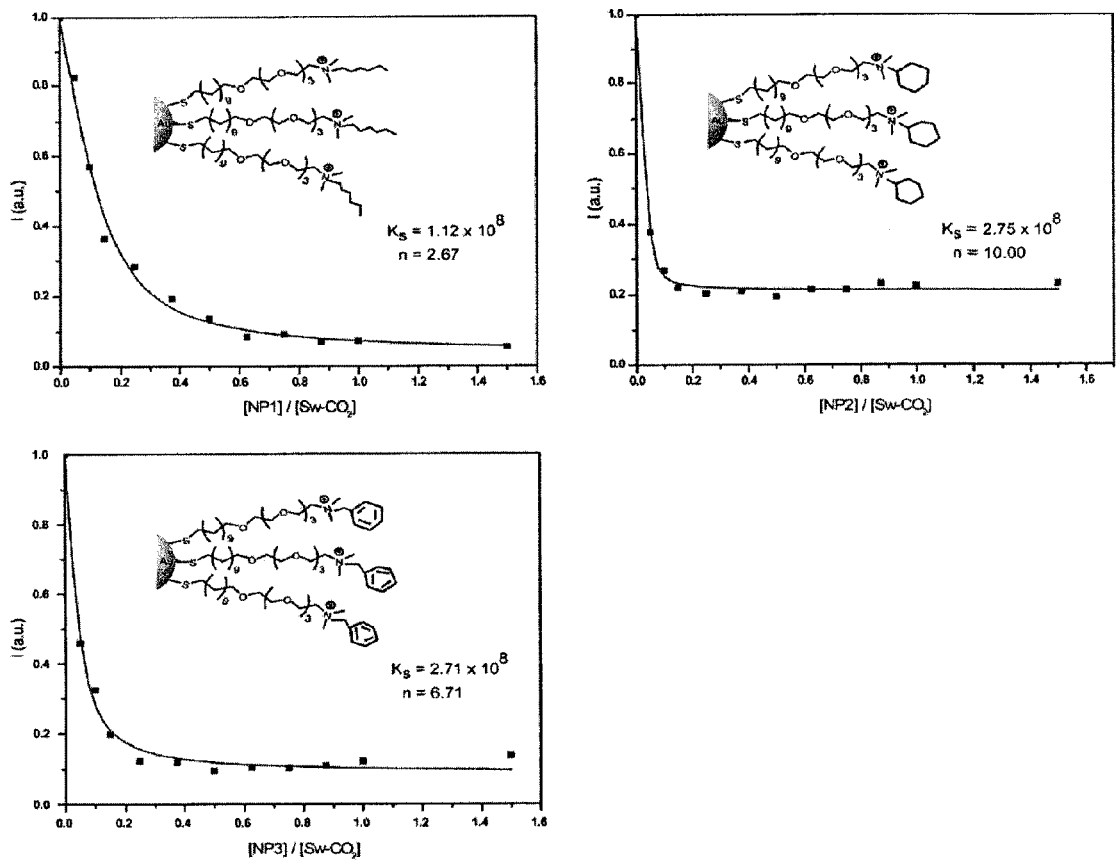
FIG. 3A. Fluorescence titration curves for the complexation of Sw-$CO_2$ (100 nM) with cationic gold nanoparticles (NP1-NP3). The changes in fluorescence intensity at 463 nm were measured following the addition of cationic nanoparticles (0-150 nM) with an excitation wavelength of 400 nm. The red solid lines represent the best curve-fitting using a calculation model of a single set of identical binding sites.
Figure 4:
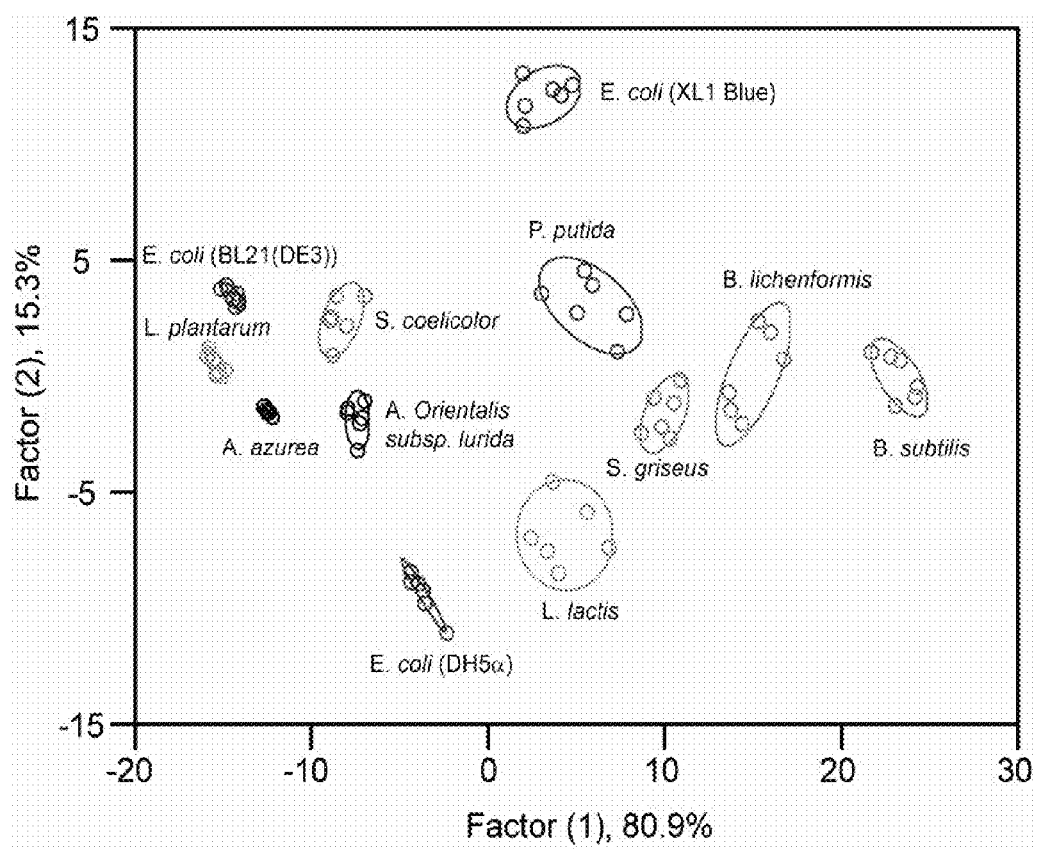
FIG. 4. Canonical score plot for the fluorescence response patterns as determined with LDA. The first two factors consist of 96.2% variance and the 95% confidence ellipse for the individual bacteria are depicted.

To demonstrate the fluorophore displacement strategy an oligo (ethylene glycol)-substituted carboxylate PPE (Sw-$CO_2$) and three hydrophobic ammonium-functionalized gold nanoparticles (NP1-NP3) were chosen to provide the sensor elements (FIG. 2). (As indicated above, various other fluoropolymers can be employed with such nanoparticles or, alternately, with nanoparticles of the sort (e.g., NP1-14) described in the aforementioned incorporated co-pending application.) Fluorescence titration studies revealed that the cationic gold nanoparticles (NP1-NP3) quench the fluorescence of Sw-$CO_2$ through formation of supramolecular complexes (see FIG. 3A and Table 1). Quenching by the nanoparticle is efficient: typically, an aqueous solution of the polymer (100 nM, based on 12 repeat units/polymer) with a stoichiometric amount of nanoparticle displays approximately 20% of the initial fluorescence of Sw-$CO_2$ ($\Phi$=0.33). The polymer and a stoichiometric amount of nanoparticles (NP1-NP3) were mixed in 5 mM phosphate buffer (pH 7.4) to yield nanoparticle-Sw-$CO_2$ constructs with final polymer and nanoparticle concentrations of 100 nM and 10-40 nM, respectively.

The exposure of these three nanoparticle-Sw-$CO_2$ constructs towards bacteria ($OD_{600}$=0.05) induced different levels of fluorescence changes (FIG. 3B). In most cases, the fluorescence of the solution increases upon addition of the microorganisms. Significantly, the fluorescence changes exhibit reproducible patterns that depend upon the strains and classes of bacteria, indicating differentiation in the fluorophore displacement. The 12 different bacteria display excellent separation when the fluorescence changes were plotted in a three-dimensional graph with the fluorescence change of the three nanoparticles (NP1-NP3) as the respective axes (FIG. 3C) explicitly demonstrating the ability of these particles to discriminate between bacteria.

In selecting nanoparticles that would constitute the sensor array, both hydrophilic and hydrophobic nanoparticles were initially tested. Upon incubation with bacteria and under the protocols employed, however, hydrophobic nanoparticle constructs (e.g., NP1-NP3) produced significant fluorescence recovery while nanoparticles with hydrophilic tails (e.g., hydroxyl groups, etc.) induced merely marginal fluorescence changes. Since these two kinds of nanoparticles exhibit comparable binding affinity to Sw-$CO_2$, the difference in the fluorescence recovery indicates that the former strongly interact with bacteria. Without limitation, a plausible explanation is that the hydrophobic parts of the nanoparticles interact with hydrophobic regions on the surface of the bacteria (e.g. the alkyl chain in teichoic acid), enhancing the electrostatic nanoparticle-bacteria interaction and, thereby, the fluorescence regeneration. Therefore, both electrostatic and hydrophobic interactions seem to play important roles in the complexation of these particles with bacteria. The engineering of the size, shape and hydrophobicity of the nanoparticle tails would provide a potent means to augment the diversity in the fluorescence response patterns.

The fluorescence response patterns were analyzed through linear discriminant analysis (LDA), a quantitative statistical method extensively used in pattern recognition. In this method, discriminant functions were deduced by maximizing the separation between classes relative to the variation within classes. As depicted in FIG. 4, LDA transformed the raw patterns to canonical scores which are clustered into 12 groups according to the individual bacteria. The jackknifed matrix (with cross-validation) in LDA reveals a 100% classification accuracy, indicating that such an approach can accurately and reliably discern all 12 microorganisms, which contain both Gram-positive (e.g. *A. azurea, B. subtilis*) and Gram-negative (e.g. *E. coli, P. putida*) species. The LDA plot does not place the Gram-negative bacteria into a particular, identifiable part of the graph, suggesting that other effects are also involved in the discrimination process. Significantly, different strains of *E. coli* can be easily discerned with the current sensor array. Again, the three *E. coli* strains are not grouped particularly close in the LDA plot, indicating that rather subtle differences in the bacteria generate marked changes in response.

With patterns of the sort shown in FIG. 3A and Table 2 as the training matrix (3 constructs×12 bacteria×6 replicates), such a sensor array can be used to identify unknown solutions of bacteria. The unknown samples were randomly selected from the 12 bacterial species grown in different batches. Fluorescence response patterns generated from the three nanoparticle-polymer constructs was characterized by LDA. After transformation of the unknown patterns to the canonical scores using the discriminant functions established on the training samples, the Mahalanobis distances of the new case to the respective centroids of 12 groups were calculated. The closer a specific data set is to the center of one group, the more likely it belongs to that group. This assignment is based on the shortest Mahalanobis distance to the 12 bacteria in a three-dimensional space (canonical factors 1 to 3). For the 64 samples studied, 61 were correctly identified, resulting in a detection accuracy of >95%. This demonstrates expedient and reliable identification of bacteria. In particular, the differentiation of the three strains of *E. coli* suggests that this methodology will be suitable for identification of pathogenic strains of normally harmless bacteria.

Regardless of the identity of any nanoparticle, fluoropolymer or analyte, this invention can be embodied by a matrix including an array of a plurality of the same or different sensor complexes on, connected with and/or coupled to a solid substrate—such as a matrix as can be utilized as or a part of a chip-based sensor, kit or related sensor apparatus for analyte detection and/or identification. For purpose of illustration only, a representative matrix can be fabricated as illustrated in FIG. 5. For example, a silicon wafer or suitable substrate material (e.g., with a hydroxylated surface) can be thiol-functionalized with an appropriate silane reagent, then coupled to gold nanoparticles. Optional ligand (e.g., citrate) protection can be removed and/or exchanged for a cationic ligand component, of the type described herein, for subsequent non-covalent fluoropolymer binding. Microspotter apparatus techniques can be used for surface and/or nanoparticle functionalization and subsequent polymer absorption. Such a surface-based protocol and assembly precludes premixing polymer with particle. Contact with a fluid medium (e.g., a biofluid possibly containing an analyte of interest) can be simply introduced to such a chip matrix, with fluorescence and/or change thereof recorded using either plate-reader technology or a suitable CCD camera.

As demonstrated with representative, non-limiting embodiments, the integration of cationic gold nanoparticles with conjugated polymers provides an easily accessible yet potentially powerful biodiagnostic tool, in which the functional nanoparticles and the fluorescent polymer serve as the recognition elements and the transducer, respectively. The efficient quenching ability of gold nanoparticles coupled with the 'molecular wire' effect of conjugated polymers compound the pronounced fluorescence response, which is dictated by the binding strength of the bacterium to the gold nanoparticle. Therefore, manipulating the surface chemistry of gold nanoparticles and the constitution of the conjugated polymer will result in constructs with expanded binding capabilities. Based on the ability to readily differentiate 12 different bacteria using only three systems, it would be understood in the art that this invention can be extended for use in the detection of a wide range of microorganisms including the differentiation of pathogenic and resistant strains.

EXAMPLES OF THE INVENTION

The following non-limiting examples and data illustrate various aspects and features relating to the methods and/or articles of the present invention, including the detection and identification of unknown pathogen species and strains. In comparison with the prior art, the present methods and/or articles provide results and data which are surprising, unexpected and contrary thereto. While the utility of this invention is illustrated through the use of several nanoparticulate sensor complexes and molecular components which can be used to therewith in the context of certain bacterial species/strains, it will be understood by those skilled in the art, that comparable results are obtainable with various other nanoparticles and fluorophore components in the detection/identification of other pathogens (e.g., viruses, fungi, etc.), as are commensurate with the scope of this invention.

Conjugated polymer (Sw-CO$_2$) and the cationic gold nanoparticles (NP1-NP3, core diameter ~2 nm) were synthesized according to published procedures. (See, examples 4 and 5 and I. B. Kim, R. Phillips, U. H. F. Bunz, *Macromolecules* 2007, 40, 5290-5293; C.-C. You, O. R. Miranda, B. Gider, P. S. Ghosh, I.-B. Kim B. Erdogan, S. A. Krovi, U. H. F. Bunz, V. M. Rotello, *Nat. Nanotechnol.* 2007, 2, 318-323.) The number average molecular weight ($M_n$=25 kDa), polydispersity index (PDI=1.8) and degree of polymerization ($P_n$=12) of Sw-CO$_2$ were determined by gel permeation chromatography. The bacterial stocks were donated by Dr. A. Bommarius (Georgia Institute of Technology) and Dr. J. Hardy (University of Massachusetts at Amherst): *Amycolatopsis azurea* (*A. azurea*), *Amycolatopsis orientalis* subsp. *lurida* (*A. orientalis* subsp. *lurida*), *Bacillus lichenformis* (*B. lichenformis*), *Bacillus subtilis* (*B. subtilis*), *Escherichia coli* (BL21 (DE3)) (*E. coli* (BL21(DE3)), *Escherichia coli* (DH5a) (*E. coli* (DH5a)), *Escherichia coli* (XL1 Blue) (*E. coli* (XL1 Blue)), *Lactococcus lactis* (*L. lactis*), *Lactococcus plantarum* (*L. plantarum*), *Pseudomonas putida* (*P. putida*), *Streptomyces coelicolor* (*S. coelicolor*), and *Streptomyces griseus* (*S. griseus*).

Bacterial cells were grown in LB medium (3 mL) at 37° C. for 16 h to an optical density of 1.0 at 600 nm. The bacterial cultures were centrifuged at 4000 rpm for 15 min and washed with phosphate buffer (5 mM, pH 7.4) three times. The bacteria were resuspended in phosphate buffer and diluted to an absorbance of 1.0 at 600 nm. Fluorescence intensity changes at 463 nm were recorded in 96-well plates (300 µL Whatman® Glass Bottom microplate) on a Molecular Devices SpectraMax M5 micro plate reader with an excitation wavelength of 400 nm.

EXAMPLE 1

Fluorescence titration experiments were conducted to evaluate the complexation between nanoparticles and Sw-CO$_2$. For recording the fluorescence response patterns in the presence of bacteria, Sw-CO$_2$ and stoichiometric amounts of NP1-NP3, as determined by the fluorescence titration study (Table 1), were diluted with phosphate buffer (5 mM, pH 7.4) to yield solutions with a final polymer (Sw-CO$_2$) concentration of 100 nM. Subsequently, each solution (200 µL) was placed into a respective well on the microplate. After incubation for 15 min, the fluorescence intensity at 463 nm was recorded with an excitation wavelength of 400 nm.

TABLE 1

Binding constants ($K_s$) and binding stoichiometries (n) between anionic polymer (Sw-CO$_2$) and three cationic nanoparticles (NP1-NP3) as determined from fluorescence titration.

| Nanoparticle | $K_s/10^8 M^{-1}$ | $-\Delta G/kJ\ mol^{-1}$ | n |
|---|---|---|---|
| NP1 | 1.12 | 45.9 | 2.67 |
| NP2 | 2.75 | 48.1 | 10.0 |
| NP3 | 2.71 | 48.1 | 6.71 |

EXAMPLE 2

Next, 10 µL of a bacterial solution (OD$_{600}$=0.05) was added to each well. After incubation for another 15 min, the fluorescence intensity at 463 nm was measured again. The fluorescence intensity before addition of bacteria was subtracted from that obtained after addition of bacteria, to record the overall fluorescence response ($\Delta I$). This process was completed for 12 bacteria to generate six replicates of each, leading to a training data matrix of 3 constructs×12 bacteria×6 replicates (Table 2) that was subjected to a classical linear discriminant analysis (LDA) using SYSTAT (version 11.0). The Mahalanobis distances of each individual pattern to the centroid of each group in a multidimensional space were calculated and the case was assigned to the group with the shortest Mahalanobis distance.

TABLE 2

Training matrix of fluorescence response patterns generated from NP-(Sw-CO$_2$) sensor array (NP1-NP3) against various types of bacteria (OD = 0.05 at 600 nm).

| Bacteria | NP1 | NP2 | NP3 |
|---|---|---|---|
| *A. azurea* | 1.320 | 8.363 | 7.758 |
| *A. azurea* | 1.875 | 8.085 | 11.318 |
| *A. azurea* | 1.643 | 6.843 | 7.628 |
| *A. azurea* | 1.810 | 8.313 | 14.915 |
| *A. azurea* | 1.283 | 7.735 | 5.742 |
| *A. azurea* | 1.305 | 9.253 | 8.243 |
| *A. orientalis* subsp. *lurida* | 30.668 | 32.533 | 25.598 |
| *A. orientalis* subsp. *lurida* | 33.398 | 35.758 | 34.093 |
| *A. orientalis* subsp. *lurida* | 31.160 | 34.170 | 37.205 |
| *A. orientalis* subsp. *lurida* | 24.005 | 42.848 | 29.438 |
| *A. orientalis* subsp. *lurida* | 29.243 | 26.558 | 38.220 |
| *A. orientalis* subsp. *lurida* | 38.018 | 29.803 | 41.178 |
| *B. lichenformis* | 195.318 | 124.438 | 140.640 |
| *B. lichenformis* | 164.993 | 136.788 | 142.965 |
| *B. lichenformis* | 163.903 | 123.355 | 154.520 |
| *B. lichenformis* | 167.495 | 120.315 | 152.213 |
| *B. lichenformis* | 194.945 | 133.145 | 158.730 |
| *B. lichenformis* | 196.840 | 125.638 | 152.393 |
| *B. subtilis* | 235.218 | 174.260 | 196.053 |
| *B. subtilis* | 232.040 | 174.323 | 198.023 |
| *B. subtilis* | 235.505 | 164.763 | 190.720 |
| *B. subtilis* | 227.188 | 153.493 | 185.988 |
| *B. subtilis* | 222.990 | 172.223 | 189.518 |
| *B. subtilis* | 232.705 | 156.003 | 198.215 |
| *E. coli* (BL21(DE3)) | 17.443 | −26.578 | −4.338 |
| *E. coli* (BL21(DE3)) | 14.325 | −28.983 | −3.265 |
| *E. coli* (BL21(DE3)) | 15.175 | −18.655 | −4.203 |
| *E. coli* (BL21(DE3)) | 16.275 | −21.973 | −2.668 |
| *E. coli* (BL21(DE3)) | 19.198 | −20.328 | −4.965 |
| *E. coli* (BL21(DE3)) | 17.968 | −19.300 | −2.903 |
| *E. coli* (DH5α) | 9.335 | 61.068 | 105.800 |
| *E. coli* (DH5α) | 11.843 | 52.365 | 109.883 |
| *E. coli* (DH5α) | 12.013 | 60.328 | 100.815 |
| *E. coli* (DH5α) | 12.360 | 55.873 | 92.673 |
| *E. coli* (DH5α) | 9.893 | 57.170 | 94.078 |
| *E. coli* (DH5α) | 9.860 | 70.608 | 116.055 |
| *E. coli* (XL1 Blue) | 158.553 | 6.858 | 105.023 |
| *E. coli* (XL1 Blue) | 171.280 | 3.700 | 90.718 |
| *E. coli* (XL1 Blue) | 164.298 | 9.120 | 94.633 |
| *E. coli* (XL1 Blue) | 177.520 | 6.280 | 115.653 |
| *E. coli* (XL1 Blue) | 185.140 | 6.520 | 128.793 |
| *E. coli* (XL1 Blue) | 178.785 | 5.023 | 126.658 |
| *L. lactis* | 83.708 | 80.135 | 123.985 |
| *L. lactis* | 63.935 | 97.958 | 129.270 |
| *L. lactis* | 61.988 | 70.870 | 145.810 |
| *L. lactis* | 88.515 | 95.460 | 133.183 |
| *L. lactis* | 64.880 | 83.260 | 140.150 |
| *L. lactis* | 87.530 | 101.368 | 153.320 |
| *L. plantarum* | −6.428 | −15.945 | −12.628 |
| *L. plantarum* | −7.400 | −10.255 | −9.813 |
| *L. plantarum* | −3.183 | −8.055 | −8.163 |
| *L. plantarum* | −4.235 | −11.848 | −13.960 |
| *L. plantarum* | −7.460 | −11.235 | −7.278 |
| *L. plantarum* | −3.730 | −16.715 | −13.028 |
| *P. putida* | 133.883 | 77.358 | 84.243 |
| *P. putida* | 138.650 | 91.008 | 104.965 |
| *P. putida* | 126.060 | 62.608 | 77.063 |
| *P. putida* | 145.825 | 73.970 | 92.140 |
| *P. putida* | 146.658 | 71.735 | 84.733 |
| *P. putida* | 150.738 | 84.933 | 109.765 |
| *S. coelicolor* | 45.600 | 14.303 | 12.790 |
| *S. coelicolor* | 38.213 | 20.615 | 16.215 |
| *S. coelicolor* | 50.170 | 21.460 | 14.265 |
| *S. coelicolor* | 46.963 | 15.608 | 10.325 |
| *S. coelicolor* | 53.710 | 10.520 | 15.943 |
| *S. coelicolor* | 63.685 | 19.250 | 21.253 |

TABLE 2-continued

Training matrix of fluorescence response patterns generated
from NP-(Sw-CO$_2$) sensor array (NP1-NP3) against various
types of bacteria (OD = 0.05 at 600 nm).

| Bacteria | NP1 | NP2 | NP3 |
|---|---|---|---|
| S. griseus | 153.198 | 100.128 | 147.823 |
| S. griseus | 135.543 | 104.763 | 142.028 |
| S. griseus | 134.793 | 94.068 | 173.475 |
| S. griseus | 139.033 | 84.893 | 162.908 |
| S. griseus | 126.708 | 96.993 | 143.033 |
| S. griseus | 144.808 | 92.060 | 166.973 |

TABLE 3

Accuracy of LDA classification of bacteria analytes (OD$_{600}$ = 0.05)
from the complexes of the fluorescent polymer (Sw-CO$_2$) with
individual cationic nanoparticles as sensors. The values are taken from
the Jackknifed classification matrix based on LDA analysis of the raw
data (6 replicates) listed in Table 2.

| Bacteria | NP1-(Sw-CO$_2$) | NP2-(Sw-CO$_2$) | NP3-(Sw-CO$_2$) | (NP1-NP3)-(Sw-CO$_2$) |
|---|---|---|---|---|
| A. azurea | 100 | 83 | 83 | 100 |
| A. orientalis subsp. lurida | 83 | 100 | 100 | 100 |
| B. lichenformis | 50 | 100 | 33 | 100 |
| B. subtilis | 100 | 100 | 100 | 100 |
| E. coli (BL21(DE3)) | 100 | 100 | 100 | 100 |
| E. coli (DH5α) | 100 | 83 | 33 | 100 |
| E. coli (XL1 Blue) | 50 | 83 | 17 | 100 |
| L. lactis | 83 | 17 | 50 | 100 |
| L. plantarum | 100 | 100 | 83 | 100 |
| P. putida | 33 | 50 | 67 | 100 |
| S. coelicolor | 67 | 83 | 83 | 100 |
| S. griseus | 50 | 67 | 33 | 100 |
| Total | 76 | 81 | 65 | 100 |

EXAMPLE 3

A similar procedure was also performed to identify 64 randomly selected bacterial samples based on their fluorescence response patterns. The classification of new cases was achieved by computing their shortest Mahalanobis distances to the groups generated through the training matrix (3 constructs (NP1-NP3)×12 bacteria×6 replicates). During the identification of unknown bacteria, the bacterial samples were randomly selected from the 12 respective bacteria and the solution preparation, data collection, and LDA analysis were each performed by different researchers, resulting in a double-blind process.

TABLE 4

Identification of 64 unknown bacterial samples with LDA
using assemblies of Sw-CO$_2$ and NP1-NP3. From the unknown bacterial
samples, 61 out of 64 were correctly identified, resulting in an accuracy of 95.3%.

| Entry | Fluorescence response pattern | | | LDA Identification | Correct Identification |
|---|---|---|---|---|---|
| | NP1 | NP2 | NP3 | Bacteria | Yes/NO |
| 1 | 142.533 | 75.388 | 92.108 | P. putida | YES |
| 2 | 182.858 | 127.943 | 149.733 | B. lichenformis | YES |
| 3 | 77.468 | 88.975 | 138.883 | L. lactis | YES |
| 4 | 30.539 | 33.934 | 34.990 | A. orientalis subsp. lurida | YES |
| 5 | 18.646 | −23.160 | −3.736 | E. coli (BL21(DE3)) | YES |
| 6 | 11.639 | 57.813 | 101.611 | E. coli (DH5α) | YES |
| 7 | 49.205 | 16.395 | 15.680 | S. coelicolor | YES |
| 8 | 141.730 | 78.216 | 92.954 | P. putida | YES |
| 9 | 174.401 | 7.234 | 109.469 | E. coli (XL1 Blue) | YES |
| 10 | 31.039 | 32.559 | 33.740 | A. orientalis subsp. lurida | YES |
| 11 | 204.689 | 153.540 | 205.669 | B. subtilis | NO |
| 12 | 232.956 | 165.099 | 192.426 | B. subtilis | YES |
| 13 | 1.955 | 7.644 | 9.180 | A. azurea | YES |
| 14 | 137.791 | 95.444 | 157.609 | S. griseus | YES |
| 15 | 182.769 | 129.653 | 151.988 | B. lichenformis | YES |
| 16 | −5.669 | −12.276 | −10.574 | L. plantarum | YES |
| 17 | 182.396 | 124.340 | 149.264 | B. lichenformis | YES |
| 18 | 17.094 | −24.721 | −4.388 | E. coli (BL21(DE3)) | YES |
| 19 | 11.456 | 56.974 | 104.551 | E. coli (DH5α) | YES |
| 20 | 30.545 | 35.691 | 32.033 | A. orientalis subsp. lurida | YES |
| 21 | 174.821 | 6.005 | 113.186 | E. coli (XL1 Blue) | YES |
| 22 | 47.008 | 17.113 | 15.470 | S. coelicolor | YES |
| 23 | 232.094 | 165.985 | 191.679 | B. subtilis | YES |
| 24 | 1.936 | 9.194 | 9.234 | A. azurea | YES |
| 25 | 11.245 | 59.013 | 102.789 | E. coli (DH5α) | YES |
| 26 | 171.610 | 5.960 | 110.973 | E. coli (XL1 Blue) | YES |
| 27 | 32.531 | 32.886 | 33.358 | A. orientalis subsp. lurida | YES |
| 28 | 140.358 | 96.693 | 155.983 | S. griseus | YES |
| 29 | 204.960 | 155.854 | 174.626 | B. subtilis | NO |
| 30 | 13.996 | −23.933 | −3.560 | E. coli (BL21(DE3)) | YES |
| 31 | 47.584 | 17.030 | 15.216 | S. coelicolor | YES |
| 32 | −4.958 | −13.494 | −11.673 | L. plantarum | YES |
| 33 | 1.496 | 8.318 | 9.690 | A. azurea | YES |

TABLE 4-continued

Identification of 64 unknown bacterial samples with LDA
using assemblies of Sw-CO₂ and NP1-NP3. From the unknown bacterial
samples, 61 out of 64 were correctly identified, resulting in an accuracy of 95.3%.

| | Fluorescence response pattern | | | LDA Identification | Correct Identification |
|---|---|---|---|---|---|
| Entry | NP1 | NP2 | NP3 | Bacteria | Yes/NO |
| 34 | −5.145 | −11.691 | −10.746 | L. plantarum | YES |
| 35 | 230.105 | 165.309 | 191.754 | B. subtilis | YES |
| 36 | 139.821 | 95.380 | 156.686 | S. griseus | YES |
| 37 | 142.581 | 75.099 | 92.426 | P. putida | YES |
| 38 | 175.360 | 6.960 | 113.460 | E. coli (XL1 Blue) | YES |
| 39 | 175.956 | 6.429 | 110.243 | E. coli (XL1 Blue) | YES |
| 40 | 177.206 | 131.679 | 153.993 | B. lichenformis | YES |
| 41 | 1.730 | 8.059 | 9.379 | A. azurea | YES |
| 42 | 143.094 | 77.610 | 91.804 | P. putida | YES |
| 43 | 176.345 | 7.005 | 109.099 | E. coli (XL1 Blue) | YES |
| 44 | 231.541 | 165.444 | 193.734 | B. subtilis | YES |
| 45 | 138.209 | 94.530 | 155.216 | S. griseus | YES |
| 46 | 179.203 | 126.666 | 151.850 | B. lichenformis | YES |
| 47 | −5.656 | −11.515 | −11.946 | L. plantarum | YES |
| 48 | 48.960 | 17.104 | 17.126 | S. coelicolor | YES |
| 49 | 50.358 | 16.068 | 15.233 | S. coelicolor | YES |
| 50 | −4.895 | −12.941 | −10.746 | L. plantarum | YES |
| 51 | 15.855 | −23.191 | −3.371 | E. coli (BL21(DE3)) | YES |
| 52 | 48.326 | 16.870 | 15.005 | S. coelicolor | YES |
| 53 | 10.729 | 61.713 | 104.940 | E. coli (DH5α) | YES |
| 54 | 15.985 | −23.040 | −3.790 | E. coli (BL21(DE3)) | YES |
| 55 | 51.345 | 17.133 | 14.724 | S. coelicolor | YES |
| 56 | 232.371 | 166.068 | 192.690 | B. subtilis | YES |
| 57 | 17.031 | −24.114 | −4.018 | E. coli (BL21(DE3)) | YES |
| 58 | 11.475 | 60.711 | 102.038 | E. coli (DH5α) | YES |
| 59 | 1.716 | 8.224 | 8.881 | A. azurea | YES |
| 60 | 174.838 | 6.734 | 115.711 | E. coli (XL1 Blue) | YES |
| 61 | 1.920 | 9.241 | 7.370 | A. azurea | NO |
| 62 | 139.838 | 95.484 | 159.461 | S. griseus | YES |
| 63 | 17.225 | −24.289 | −2.963 | E. coli (BL21(DE3)) | YES |
| 64 | 11.541 | 60.444 | 102.609 | E. coli (DH5α) | YES |

EXAMPLE 4

Synthesis of monomer 5

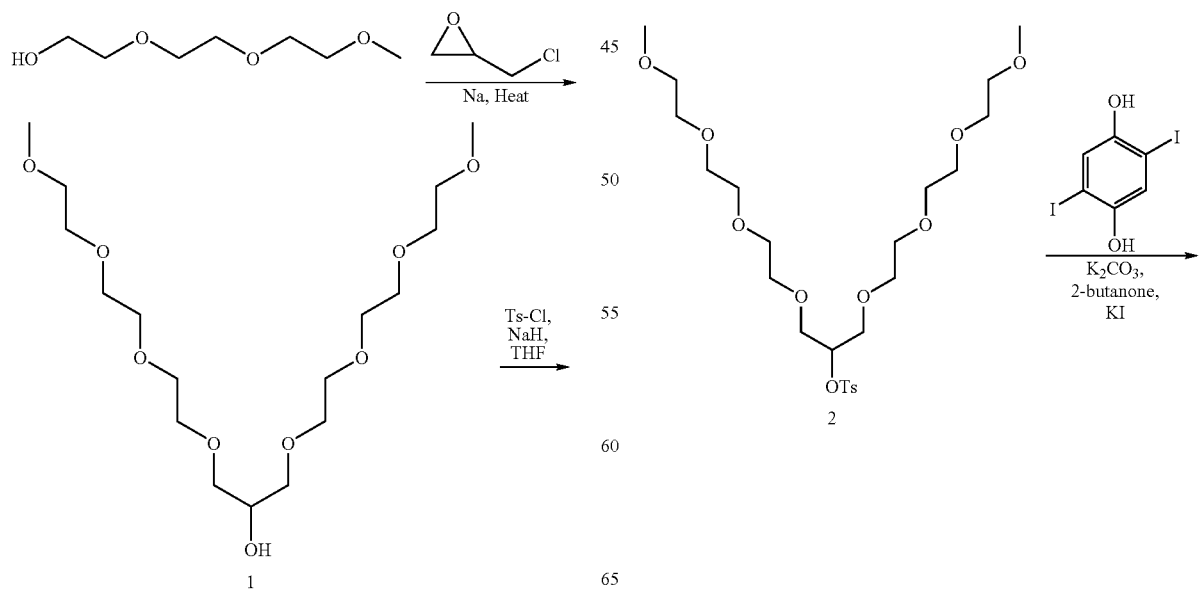

-continued

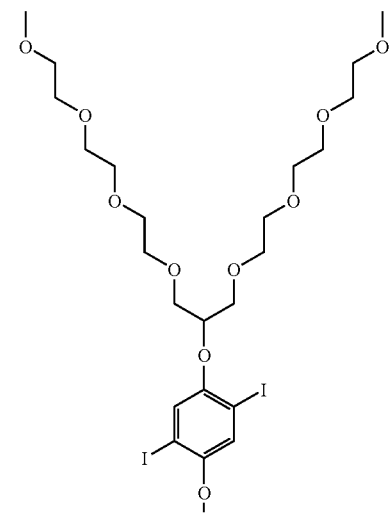

3

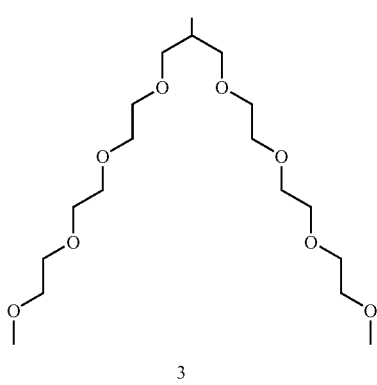

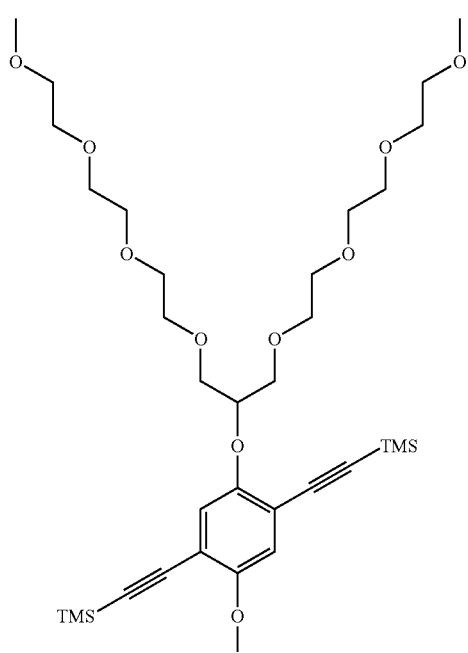

-continued

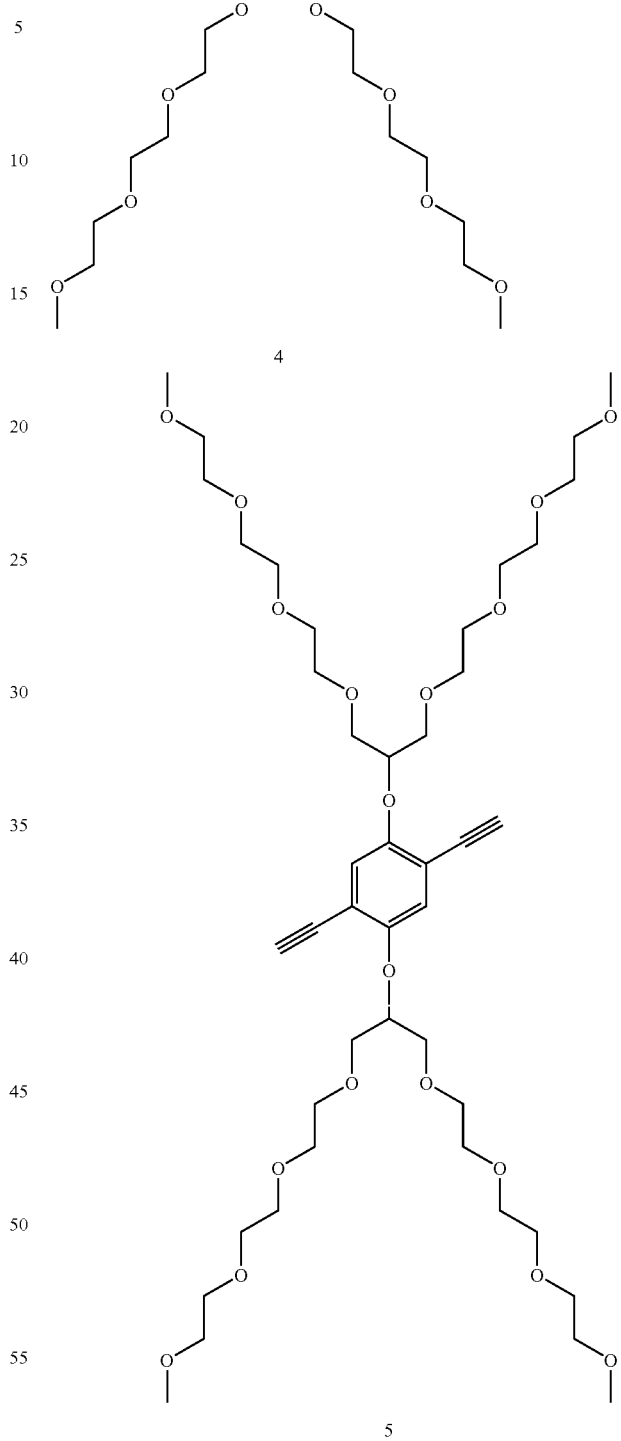

Synthesis of 1. Triethyleneglycol-monomethylether (200 g, 1.22 mol) was added to a dry 1000 mL Schlenk flask. While under $N_2$ at 100° C., Na metal (10.0 g, 0.440 mol) was added slowly and stirred until all Na metal had reacted. Upon reaction of Na, solution was cooled to 65° C., and epichlorohydrin (37.0 g, 0.400 mol, 31.4 mL) was added drop-wise. Upon complete addition of epichlorohydrin, reaction mixture was heated to 100° C., and allowed to react for 3 days. After completion of the reaction, $NH_4Cl$ (0.400 mol, 24.1 g) was added and reacted at 100° C. for 1 h. The reaction was cooled to room temperature, filtered to remove excess salts, and purified by distillation. The first fraction contained excess starting material, while the second fraction contained product as a light yellowish oil (70.2 g, 0.182 mol, 45.6%).

Synthesis of 2. Compound 1 (15.0 g, 0.0390 mol) was dissolved in dry THF (250 mL). While under $N_2$, the solution was cooled to 0° C. and NaH (1.2 eq, 0.0468 mol, 1.12 g) was added. Upon cessation of $H_2$, Ts-Cl (0.0390 mol, 7.43 g) was dissolved in dry THF (50 mL) and added to the previous solution. The reaction mixture was warmed to room temperature and reacted overnight. The resulting solution was filtered, the solvent was removed, and the crude oil was dried on the pump. The product was purified by silica gel chromatography (10:1 EtOAc/MeOH). The product was an orange oil (15.1 g, 0.0279 mol, 71.6%).

Synthesis of 3. A suspension of 1,4-dihydroxy-2,5-diiodobenzene (5.01 g, 0.0138 mol), compound 2 (15.0 g, 0.0278 mol), and $K_2CO_3$ (4 eq., 7.64 g, 0.0553 mol) were dissolved in a minimal amount of 2-butanone (75 mL) and heated to reflux. A small amount of KI was added to promote the reaction by exchanging with tosylate. The mixture was reacted for 5 days. The reaction mixture was cooled to room temperature, diluted with $CH_2Cl_2$ (250 mL), and filtered with celite to remove the black insoluble residue. The solution was concentrated in vacuo to remove the solvent and the crude oil was purified by silica gel chromatography (90:10 EtOAc/MeOH) yielding a viscous orange oil (6.20 g, 0.00567 mol, 41.0%).

Synthesis of 4. Compound 3 (4.61 g, 4.11 mmol) was dissolved in dry THF (5 mL) and stirred under $N_2$ for 15 min. Upon degassing, CuI (0.01 eq., 0.042 mmol, 8.1 mg), $(PPh_3)_2PdCl_2$ (0.01 eq., 0.042 mmol, 29.5 mg), piperidine (5 mL), and TMS-acetylene (4 eq., 16.8 mmol, 2.39 mL) were all added to the reaction. The reaction was stirred at room temperature for 2 d. The reaction mixture was diluted with THF (25 mL) and filtered to remove any excess salts. The solvent was removed and the crude product was purified by silica gel chromatography (9:1 EtOAc/MeOH). The resulting product was an orange oil (3.62 g, 3.40 mmol, 83.0%).

Synthesis of 5. Compound 4 (3.62 g, 3.40 mmol) was dissolved in MeOH (50 mL). KF (4 eq., 1.07 g, 0.0140 mol) was dissolved in MeOH (25 mL) and added to the previous solution. The reaction was stirred overnight at room temperature. The solvent was removed and the crude product was re-dissolved in $CHCl_3$. The solution was extracted with $H_2O$ and the organic fractions were collected and concentrated in vacuo. The crude product was purified by silica gel chromatography (10:1 EtOAc/MeOH) which resulted in an orange oil (2.64 g, 2.96 mmol, 87.1%).

EXAMPLE 5

Synthesis of polymer 7

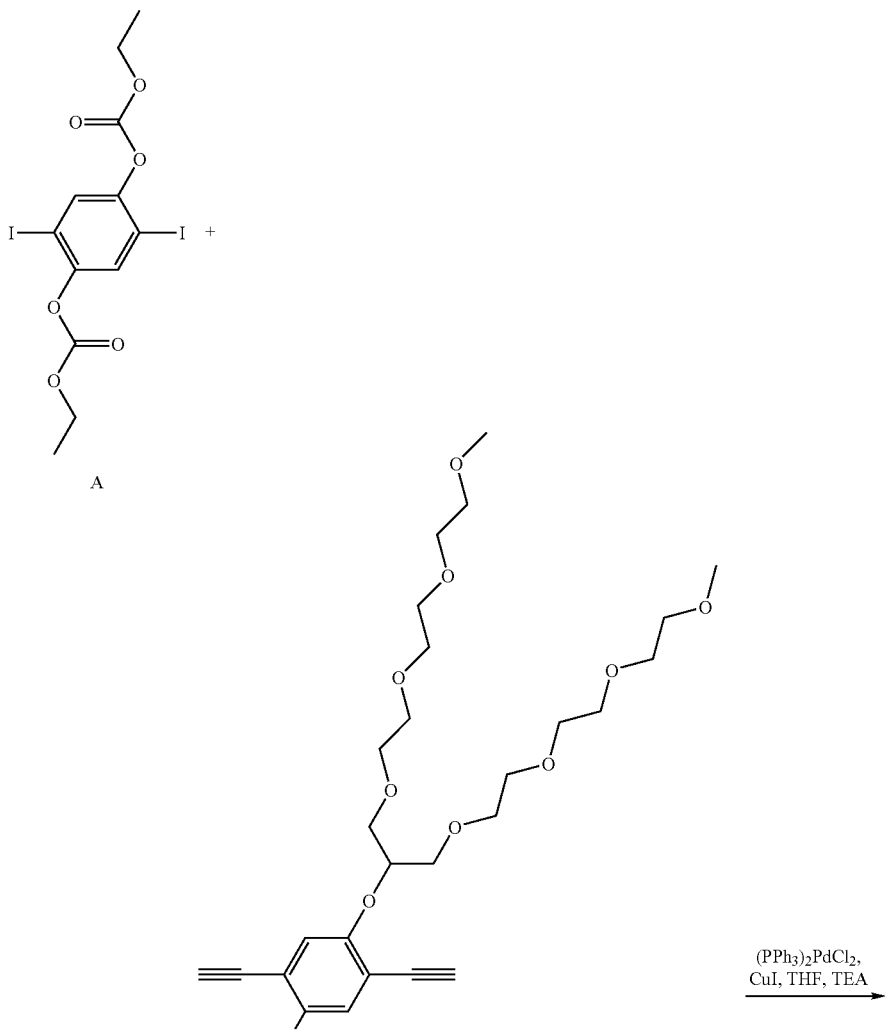

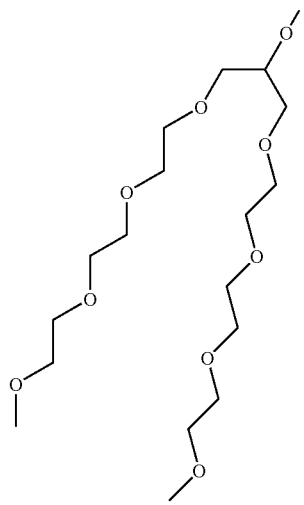
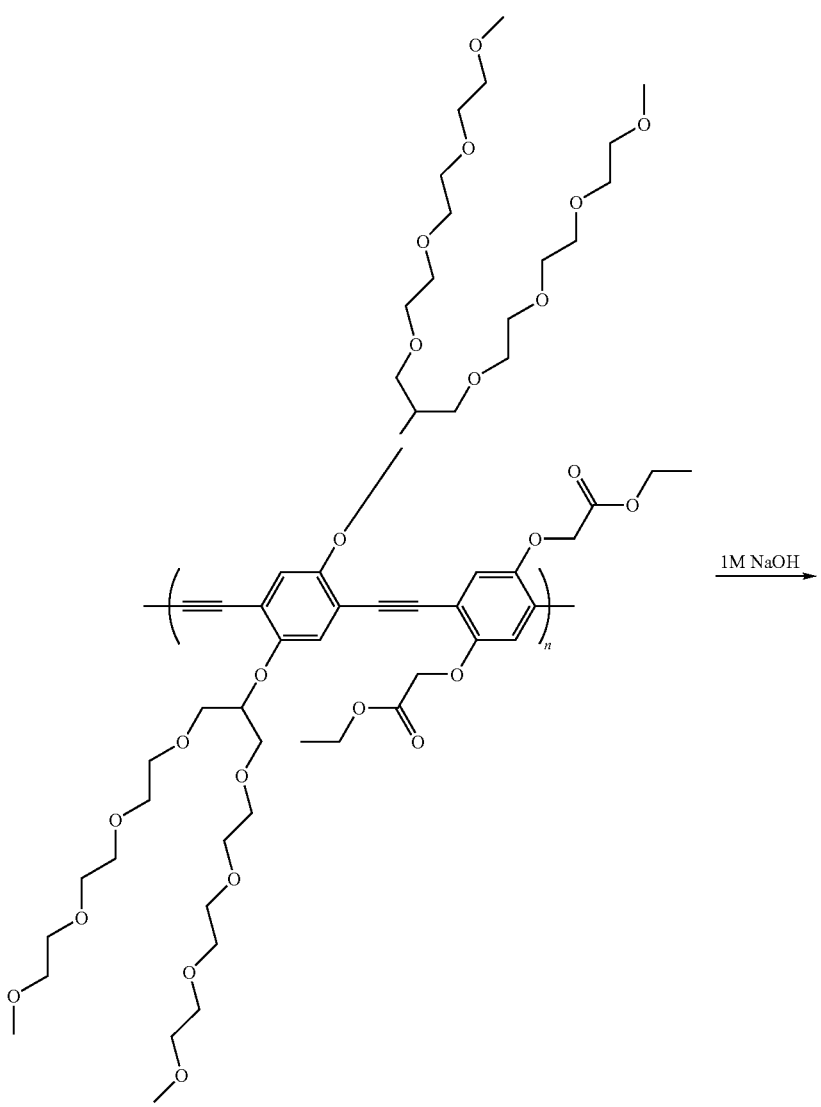

-continued

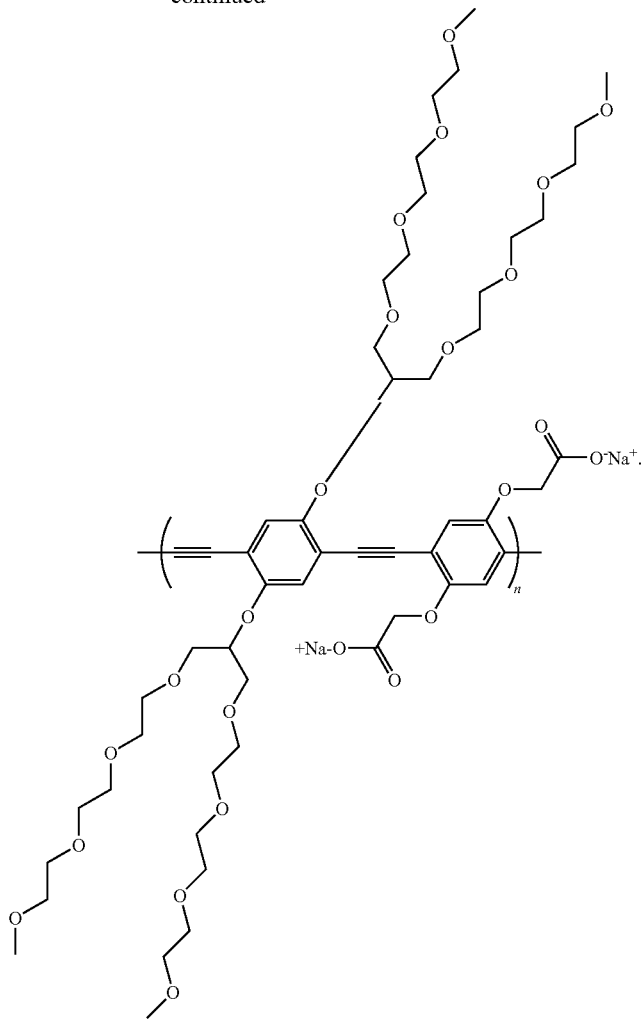

7

Synthesis of polymer 6: Compound 5 (890 mg, 1 mmol), compound A (534 mg, 1 mmol), THF (3 mL), and TEA (3 mL) were all combined in a 25 mL Schlenk tube. Upon degassing, $(PPh_3)_2PdCl_2$ (0.5 mol %, 3.51 mg), and CuI (1 mol %, 1.91 mg) were added to the mixture under $N_2$ and allowed to react for 2 d. The solvent was removed under vacuum and the polymer was re-dissolved in $CHCl_3$. The polymer solution was extracted with $H_2O$ (3×), the organic fractions were collected, and the solvent was removed which resulted in an orange solid (680 mg, 0.60 mmol, 60%). GPC (vs. polystyrene standards in chloroform): $M_n$, =25,211, $M_w/M_n$=1.837, n=21.

Synthesis of polymer 7: Polymer 6 (660 mg, 0.56 mmol) was deprotected in 1M NaOH and EDTA (250 mg) was added to complex any residual copper. The resulting solution was neutralized with 1M HCl, dialyzed against DI $H_2O$ for 3 d, and the solvent was removed resulting in a dark orange flaky solid.

EXAMPLE 6a

As discussed above, various other fluoropolymers can be used in conjunction with present nanoparticles and detection methods. With reference to FIG. 2A of the aforementioned application, carboxylate-substituted PPE (PPE-$CO_2$) was synthesized according to a known procedure. (Bunz, U. H. F. Synthesis and structure of PAEs. Adv. Polym. Sci. 177, 1-52 (2005); Zheng, J. & Swager, T. M. Poly(arylene ethynylene)s in chemosensing and biosensing. Adv. Polym. Sci. 177, 151-179 (2005); Kim, I -B, Dunkhorst, A., Gilbert, J. & Bunz, U. H. F. Sensing of lead ions by a carboaxlate-substituted PPE: multivalency effects. Macromolecules 38, 4560-4562 (2005).) The weight- and number-average molecular weights of the polymer are 6,600 and 3,500, respectively. The polydispersity index and degree of polymerization of the conjugated polymer are 1.88 and 12, respectively. Thiol ligands bearing ammonium end groups were synthesized through the reaction of 1,1,1-triphenyl-14,17,20,23-tetraoxa-2-thiapentacosan-25-yl methanesulphonate with corresponding substituted N,N-dimethylamines followed by deprotection in the presence of trifluoroacetic acid and triisopropylsilane. Subsequent place-exchange reaction with pentanethiol-coated gold nanoparticles (d≈2 nm) resulted in cationic gold nanoparticles NP1-NP6 in high yields. (See, example 5, below, and Brust, M., Walker, M., Bethell, D, Schiffrin, D. J. & Whyman, R. Synthesis of thiol-derivatised gold nanoparticles in a two-phase liquid-liquid system. J. Chem. Soc., Chem. Commun. 801-802 (1994).) $^1H$ NMR spectroscopic investigation revealed that the place-exchange reaction proceeds almost quantitatively and the coverage of cationic ligands on the nanoparticles is near unity.

EXAMPLE 6b

Expression and Purification of GFP. An alternate fluorophoric polymer useful in the context of this invention is green fluorescence protein (GFP), which was expressed according to standard procedures using *E. coli*. The Mw and pI of the expressed GFP is 26.9 KDa and 5.92 respectively. The maximum $\lambda_{ex}$ and $\lambda_{em}$, are 490 nm and 510 nm. (See, e.g., FIGS. 6A-B of the aforementioned co-pending incorporated application. Starter cultures from a glycerol stock of GFP in BL21 (DE3) was grown overnight in 50 ml of 2_YT media with 50 μl of 1000 m ampicilin (16 g tryptone, 10 g yeast extract, 5 g NaCl in 1 L water). The cultures were shook overnight at 250 rpm at 37° C. The following day, 5 ml of the starter cultures was added to a Fernbach flask containing 1 L of 2_YT and 1 ml 1000__ amplicilin and shook until the $OD_{600}$=0.7. The culture was then induced by adding IPTG (1 mM final concentration) and shook at 28° C. After three hours, the cells were harvested by centrifugation (5000 rpm for 15 minutes at 4° C.). The pellet was then resuspended in lysis buffer (2 mM Imidizole, 50 mM $NaH_2PO_4$, 300 mM NaCl). The cells were lysed using a microfluidizer. Once lysed, the solution was pelleted at 15000 rpm for 45 minutes at 4° C. The supernatant was further purified using HisPur Cobalt columns from Pierce (cat. Number 89969).

EXAMPLE 7

Synthesis of cationic gold nanoparticles 4

General procedure: Compound 2 bearing ammonium end groups were synthesized through the reaction of 1,1,1-triphenyl-14,17,20,23-tetraoxa-2-thiapentacosan-25-yl methanesulphonate (1) with corresponding substituted N,N-dimethylamines at ~35° C. for 48 h. The trityl protected thiol ligand (2) was dissolved in dry DiChloroMethane (Methylene Chloride, DCM) and an excess of trifluoroacetic acid (TFA, ~20 equivalent) was added. The color of the solution was turned to yellow immediately. Subsequently, triisopropylsilane (TIPS, ~1.2 equivalent) was added to the reaction mixture. The reaction mixture was stirred at room temperature for ~5 h under Ar atmosphere. The solvent and most TFA and TIPS were distilled off under reduced pressure. The pale yellow residue was washed thoroughly with hexanes and further dried in high vacuum. The product formation was quantitative and their structure was confirmed by $^1H$ NMR. Subsequent place-exchange reaction of compound 3 dissolved in DCM with pentanethiol-coated gold nanoparticles (d~2 nm) was carried out at ambient temperature for 3 days. Then, DCM was evaporated under reduced pressure. The residue was dissolved in a small amount of distilled water and dialyzed (membrane MWCO=1,000) to remove excess ligands, acetic acid and the other salts present with the nanoparticles. After dialysis, the particles were lyophilized to afford a brownish solid. The particles are redispersed in deionized water (18 MΩ-cm). $^1H$ NMR spectra in $D_2O$ showed substantial broadening of the proton signals and no free ligands were observed.

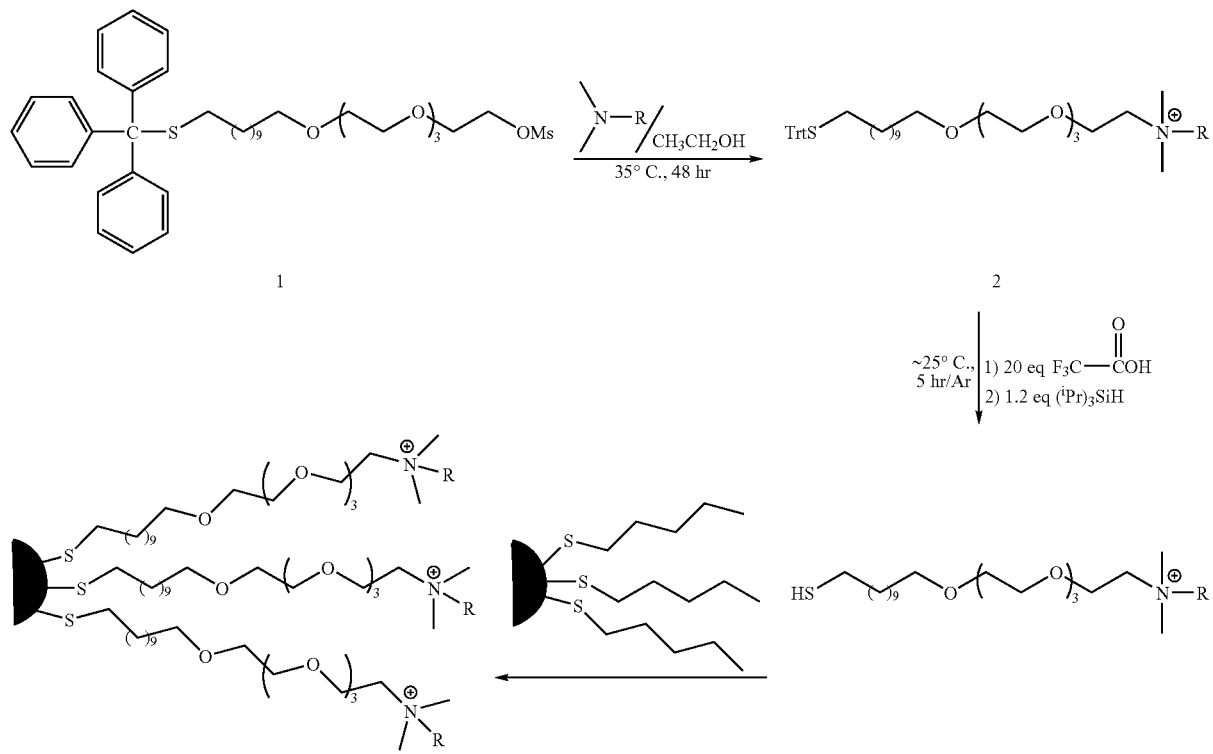

EXAMPLE 8a

Synthesis of alternate ligands

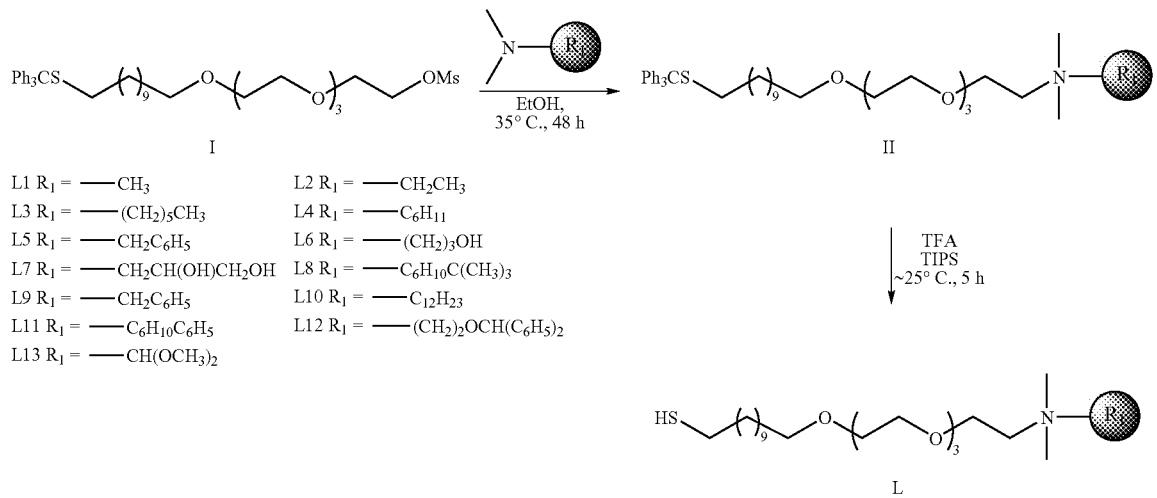

L1 R₁ = —CH₃
L2 R₁ = —CH₂CH₃
L3 R₁ = —(CH₂)₅CH₃
L4 R₁ = —C₆H₁₁
L5 R₁ = —CH₂C₆H₅
L6 R₁ = —(CH₂)₃OH
L7 R₁ = —CH₂CH(OH)CH₂OH
L8 R₁ = —C₆H₁₀C(CH₃)₃
L9 R₁ = —CH₂C₆H₅
L10 R₁ = —C₁₂H₂₃
L11 R₁ = —C₆H₁₀C₆H₅
L12 R₁ = —(CH₂)₂OCH(C₆H₅)₂
L13 R₁ = —CH(OCH₃)₂

General procedure: Compound II bearing ammonium end groups were synthesized through the reaction of 1,1,1-triphenyl-14,17,20,23-tetraoxa-2-thiapentacosan-25-yl methanesulphonate (I) with corresponding substituted N,N-dimethylamines at ~35° C. for 48 h. The trityl protected thiol ligand (II) was dissolved in dry DiChloroMethane (Methylene Chloride, DCM) and an excess of trifluoroacetic acid (TFA, ~20 equivalents) was added. The color of the solution was turned to yellow immediately. Subsequently, triisopropylsilane (TIPS, ~1.2 equivalents) was added to the reaction mixture. The reaction mixture was stirred for ~5 h under Ar condition at room temperature. The solvent and most TFA and TIPS were distilled off under reduced pressure. The pale yellow residue was washed thoroughly with hexanes and further dried in high vacuum. The product (L) formation was quantitative and their structure was confirmed by $^1$H NMR. The yields were >95%.

Compound L1: $^1$H NMR (400 MHz, CDCl₃, TMS): δ 3.95 (br, 2H, —CH₂N—), 3.70-3.58 (m, 14H, —CH₂O—+—OCH₂—(CH₂N)—), 3.49 (t, 2H, —CH₂O—), 3.25 (s, 9H, —N(CH₃)₃), 2.90 (s, 3H, —CH₃SO⁻₃—), 2.52 (q, 2H, —CH₂S—), 1.64-1.51 (m, 4H, (SCH₂)CH₂+—CH(CH₂O)—), 1.36-1.22 (m, 15H, —SH+—CH₂—).

Compound L2: $^1$H NMR (400 MHz, CDCl₃, TMS): δ 3.94 (br, 2H, —CH₂N—), 3.69-3.56 (m, 14H, —CH₂O—+—OCH—(CH₂N)—), 3.44 (t, 2H, —CH₂O—), 3.40-3.32 (m, 2H, —NCH₂—), 3.23 (s, 6H, —(CH₃)₂N—), 2.78 (s, 3H, —CH₃SO⁻₃—), 2.51 (q, 2H, —CH₂S—), 1.69-1.149 (m, 4H, (SCH₂)CH₂+—CH₂(CH₂O)—), 1.44-1.24 (m, 18H, —SH+—CH₂—+—(NCH₂)CH₃).

Compound L3: $^1$H NMR (400 MHz, CDCl₃, TMS): δ 3.95 (br, 2H, —CH₂N—), 3.68-3.56 (m, 14H, —CH₂O—+—OCH₂—(CH₂N)—), 3.46 (t, 2H, —CH₂O—), 3.40-3.33 (m, 2H, —NCH₂—), 3.19 (s, 6H, —(CH₃)₂N—), 2.87 (s, 3H, —CH₃SO⁻₃—), 2.52 (q, 2H, —CH₂S—), 1.76-1.53 (m, 6H, —(NCH₂)CH₂—)+(SCH₂)CH₂+—CH₂(CH₂O)—), 1.41-1.22 (m, 21H, —SH+—(NCH₂CH₂—)CH₂—)+—CH₂—), 0.89 (t, 3H, —CH₃—).

Compound L4: $^1$H NMR (400 MHz, CDCl₃, TMS): δ 3.95 (br, 2H, —CH₂N—), 3.81-3.72 (m, 1H, H$_{Cyclo}$), 3.69-3.53 (m, 14H, —CH₂O—+—OCH₂—(CH₂N)—), 3.49 (t, 2H, —CH₂O—), 3.11 (s, 6H, —(CH₃)₂N—), 2.91 (s, 3H, —CH₃SO⁻₃—), 2.52 (q, 2H, —CH₂S—), 2.23 (d, 2H, H$_{Cyclo}$), 1.99 (d, 2H, H$_{Cyclo}$), 1.78-1.52 (m, 4H, —(SCH₂)CH₂+—CH₂(CH₂O)—), 1.51-1.12 (m, 21H, SH+—CH2—+H$_{Cyclo}$).

Compound L5: $^1$H NMR (400 MHz, CDCl₃, TMS): δ 8.37 (d, 1H, H$_{Ar}$), 7.98 (d, 1H, H$_{Ar}$), 7.69-7.61 (m, 3H, H$_{Ar}$), 7.59-7.48 (m, 1H, H$_{Ar}$), 4.38 (br, 2H,—NCH₂—Ar)), 3.76 (br, 2H, —CH₂N—) 3.72-3.62 (m, 14H, —CH₂O—+—OCH₂—(CH₂N)—), 3.61-3.55 (m, 2H, —CH₂O—), 3.23 (s, 6H, —(CH₃)₂N—), 3.07 (s, 3H, —CH₃SO⁻₃—), 2.52 (q, 2H, —CH₂S—), 1.67-1.51 (m, 4H, —(SCH₂)CH₂+—CH₂(CH₂O)—), 1.35-1.21 (m, 15H, —SH+—CH₂—).

Compound L6: $^1$H NMR (400 MHz, CDCl₃, TMS): δ 3.94 (br, 2H, —CH₂N—), 3.75-3.52 (m, 16H, —CH₂O—+—OCH₂—(CH₂N)—+—CH₂—OH), 3.48 (t, 2H, —CH₂O—), 3.39-3.31 (m, 2H,—NCH₂—), 3.25 (s, 6H, —(CH₃)₂N—), 3.2 (br, 1H, —OH), 2.89 (s, 3H, —CH₃SO⁻₃—), 2.52 (q, 2H, —CH₂S—), 2.35-2.26 (m, 2H, —(NCH₂)CH²—), 1.70-1.52 (m, 4H, +(SCH₂)CH₂+—CH₂(CH₂O)—), 1.36-1.21 (m, 15H, —SH+—CH₂—).

Compound L7: $^1$H NMR (400 MHz, CDCl₃, TMS): δ 4.78 (br, 1H, —CHOH(CH2OH)—), 4.59 (br, 1H, —CH2OH—), 4.50-4.45 (m, 1H, —CHOH(CH2OH)—), 4.43 (d and br, 2H, —NCH₂—), 3.95 (d and br, 2H, —CH₂N—), 3.86-3.76 (d and br, 2H, —CH₂—OH), 3.75-3.55 (m, 14H, —CH₂O—+—OCH₂—(CH₂N)—), 3.48 (t, 2H, —CH₂O—), 3.34 (s, 6H, —(CH₃)₂N—), 2.99 (s, 3H, —CH₃SO⁻₃—), 2.52 (q, 2H, —CH₂S—), 1.71-1.51 (m, 4H, +(SCH₂)CH₂+—CH²(CH₂O)—), 1.42-1.21 (m, 15H, —SH+—CH₂—).

Compound L8: $^1$H NMR (400 MHz, CDCl₃, TMS): δ 3.96 (br, 2H, —CH₂N—), 3.79-3.75 (m, 1H, H$_{Cyclo}$), 3.66-3.57 (m, 14H, —CH₂O—+—OCH₂—(CH₂N)—), 3.46 (t, 2H, —CH₂O—), 3.12 (s, 6H, —(CH₃)₂N—), 2.89 (s, 3H, —CH₃SO⁻₃—), 2.52 (q, 2H, —CH₂S—), 2.28 (d, 2H, H$_{Cyclo}$), 2.01 (d, 2H, H$_{Cyclo}$), 1.64-1.54 (m, 4H, —(SCH₂)CH₂+—CH₂(CH₂O)—), 1.47 (q, 2H, H$_{Cyclo}$), 1.33 (t, $^3$J=8.0 Hz, 1H, —SH), 1.30-1.22 (m, 14H, —CH2—), 1.16 (q, 2H, H$_{Cyclo}$) 1.04 (td, 1H —CHC—), 0.86 (s, 9H, —C(CH₃)₃—).

Compound L9: $^1$H NMR (400 MHz, CDCl₃, TMS): δ 7.82 (d, 2H, H$_{Ar}$), 7.66-7.51 (m, 3H, H$_{Ar}$), 4.24 (br, 2H, —CH₂N—), 3.78 (s, 6H, —(CH₃)₂N—), 3.68-3.52 (m, 14H, —CH₂O—+—OCH₂—(CH₂N)—), 3.47-3.36 (m, 2H, —CH₂O—), 2.87 (s, 3H, —CH₃SO⁻₃—), 2.52 (q, 2H, —CH₂S—), 1.70-1.46 (m, 4H, —(SCH₂)CH₂+—CH₂(CH₂O)—), 1.42-1.1.16 (m, 15H, —SH+—CH₂—).

Compound L10: ¹H NMR (400 MHz, CDCl₃, TMS): δ 3.98 (br, 2H, —CH₂N—), 3.78-3.75 (m, 1H, H_{Cyclo}), 3.64-3.55 (m, 14H, —CH₂O—+—OCH₂—(CH₂N)—), 3.46-3.42 (dt, 2H, —CH₂O—), 3.16 (s, 6H, —(CH₃)₂N—), 2.86 (s, 3H, —CH₃SO⁻₃—), 2.52 (q, 2H, —CH₂S—), 1.93-1.40 (m, 26H, SCH₂)CH₂+—CH₂(CH₂O)—+H_{Cyclo}), 1.33 (t, ³J=7.82 Hz, 1H, —SH), 1.29-1.24 (m, 14H, —CH2—).

Compound L11: ¹H NMR (400 MHz, CDCl₃, TMS): δ 7.4-7.2 (m, 4H, H_{Ar}), 7.17 (d, 1H, H_{Ar}), 3.95 (d and br, 2H, —CH₂N—), 3.79-3.52 (m, 14H, —CH₂O—+—OCH₂—(CH₂N)—), 3.45 (q, 2H, —CH₂O—), 3.29-3.22 (m and br, 1 H, H_{Cyclo}), 3.01-2.92 (m and br, 1H, H_{Cyclo}) 2.87 (s, 3H, —CH₂S—), 1.60-1.48 (m, 4H, —(SCH₂)CH₂+—CH₂(CH₂O)—), 1.34-1.16 (m, 15H, —SH+—CH₂—).

Compound L13: ¹H NMR (400 MHz, CDCl₃, TMS): δ 3.96 (br, 2H, —CH₂N—), 3.72 (s, 1H, —(CH₃)₂NCH—), 3.70-3.53 (m, 14H, —CH₂O—+—OCH₂—(CH₂N)—), 3.46 (t, 2H, —CH₂O—), 3.33 (s, 6H, —CH(OCH₃)₂), 3.28 (s, 6H, —(CH₃)₂N—), 2.89 (s, 3H, —CH₃SO⁻₃—), 2.51 (q, 2H, —CH₂S—), 1.69-1.53 (m, 4H, (SCH₂)CH₂+—CH₂(CH₂O)—), 1.40-1.23 (m, 15H, —SH+—CH₂—+(NCH₂)CH₃).

EXAMPLE 8b

Synthesis of Ligand L14

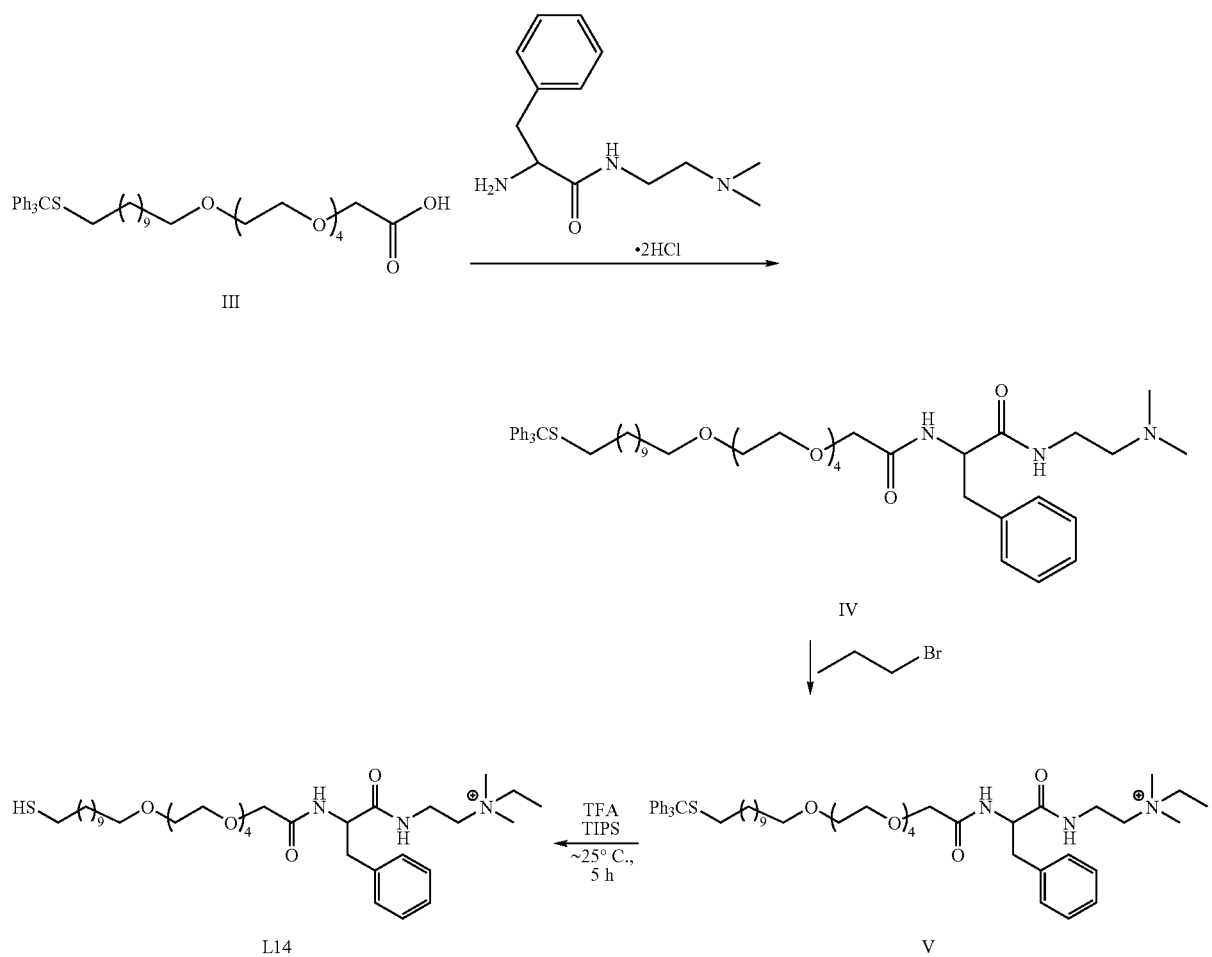

—CH₃SO⁻₃—), 2.81 (d and br, 6H, —(CH₃)₂N—), 2.52 (q, 2H, —CH₂S—), 2.39-2.26 (m, 2H, H_{Cyclo}), 2.19-2.06 (m, 2H, H_{Cyclo}), 1.96-1.84 (m, 4H, H_{Cyclo}), 1.72-1.53 (m, 4H, —(SCH₂)CH₂+—CH₂(CH₂O)—), 1.42-1.1.19 (m, 15H, —SH+—CH₂—).

Compound L12: ¹H NMR (400 MHz, CDCl₃, TMS): δ 7.42 (d, 2H, H_{Ar}), 7.37-2.27 (m, 8H, H_{Ar}), 7.25-7.18 (t, 2H, H_{Ar}), 5.13 (s, 1H, H_{Ar}), 4.12 (br, 2H, —CH₂N—)), 3.96 (br, 2H, —NCH₂(CH₂OCAr), 3.64-3.51 (m, 14H, —CH₂O—+—OCH₂—(CH₂N)—), 3.45 (t, 2H, —CH₂O—), 3.29-3.34 (m, 2H, —CH₂OCAr—), 3.28 (s, 6H, —(CH₃)₂N—), 2.86 (s, 3H, —CH₃SO⁻₃—), 2.52 (q, 2H, Procedure: Compound IV bearing L-Phe group was synthesized through the reaction of 1,1,1-triphenyl-14,17,20,23,26-pentaoxa-2-thiaoctacosan-28-oic acid (III) with corresponding 2-amino-N-(2-(dimethylamino)ethyl)-3-phenylpropanamide. Briefly, compound III was dissolved in a mixture of dry DCM and DMF that was placed in an ice-bath. When the temperature reached about 0° C., corresponding L-phenylaline derivative, 1-ethyl-3-(3-dimethylaminopropyl)carbodiimide (EDC), N-hydroxybenzotriazole (HOBt), and sodium bicarbonate were added. The mixture was stirred at room temperature for 24 h. Subsequently, the solution was poured into water and extracted with ethyl acetate (EtOAc).

The organic layers were combined and washed successively with saturated sodium bicarbonate and brine. After drying over sodium sulfate, the solvent was removed under reduced pressure. The residue was charged on SiO$_2$ column for purification. EtOAc/MeOH (90:10) and EtOAc/MeOH/NH$_4$OH (90:10:1) were used as gradient eluent. Compound V was obtained through nucleophilic substitution of compound IV with bromoethane. The trityl protected thiol ligand (V) was dissolved in dry DCM. TFA and TIPS were added successively. The reaction mixture was stirred at room temperature for ~5 h. Subsequently, the solvent was removed under reduced pressure. The residue was washed thoroughly with diethyl ether to remove the residual TFA and TIPS. After drying in high vacuum, the product L14 (5-benzyl-N-ethyl-32-mercapto-N,N-dimethyl-4,7-dioxo-9,12,15,18,21-pentaoxa-3,6-diazadotriacontan-1-aminium) was obtained in quantitative yield. Its structure was confirmed by $^1$H NMR.

Compound L14: $^1$H NMR (400 MHz, CDCl$_3$, TMS): δ 8.48 (br t, 1H, —NH—), 7.65 (br d, 1H, —NH—), 7.25 (m, 5H, H$_{Ar}$), 4.61 (m, 1H, —CH<), 4.03 (q, 2H, —OCH$_2$—), 3.8~3.4 (m, 22H, —OCH$_2$—+—CH$_2$—), 3.14 (m, 2H, —CH$_2$Ar), 3.11 (s, 6H, —CH$_3$), 2.90 (m, 2H, —CH$_2$—), 2.52 (q, 2H, —SCH$_2$—), 1.58 (m, 4H, —CH$_2$—), 1.26 (m, 17H, —CH$_2$—+—CH$_3$).

Fabrication of Cationic Gold Nanoparticles.

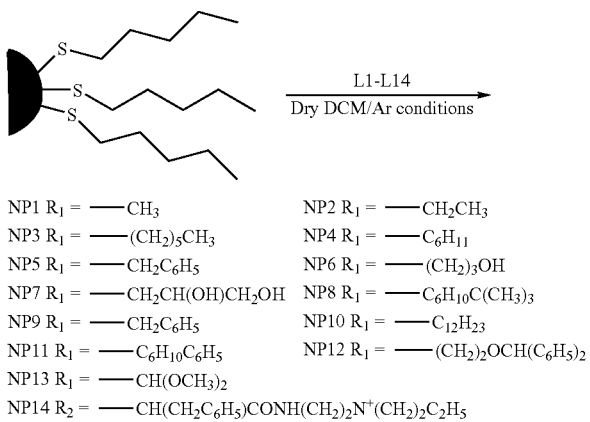

NP1 R$_1$ = —CH$_3$
NP2 R$_1$ = —CH$_2$CH$_3$
NP3 R$_1$ = —(CH$_2$)$_5$CH$_3$
NP4 R$_1$ = —C$_6$H$_{11}$
NP5 R$_1$ = —CH$_2$C$_6$H$_5$
NP6 R$_1$ = —(CH$_2$)$_3$OH
NP7 R$_1$ = —CH$_2$CH(OH)CH$_2$OH
NP8 R$_1$ = —C$_6$H$_{10}$C(CH$_3$)$_3$
NP9 R$_1$ = —CH$_2$C$_6$H$_5$
NP10 R$_1$ = —C$_{12}$H$_{23}$
NP11 R$_1$ = —C$_6$H$_{10}$C$_6$H$_5$
NP12 R$_1$ = —(CH$_2$)$_2$OCH(C$_6$H$_5$)$_2$
NP13 R$_1$ = —CH(OCH$_3$)$_2$
NP14 R$_2$ = —CH(CH$_2$C$_6$H$_5$)CONH(CH$_2$)$_2$N$^+$(CH$_2$)$_2$C$_2$H$_5$

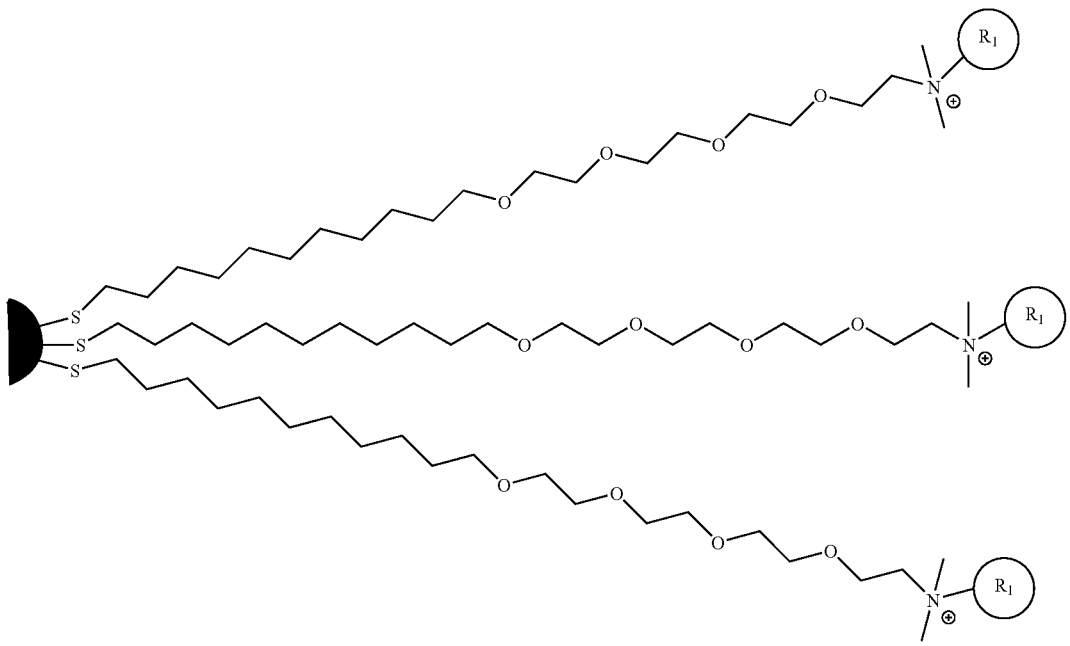

-continued

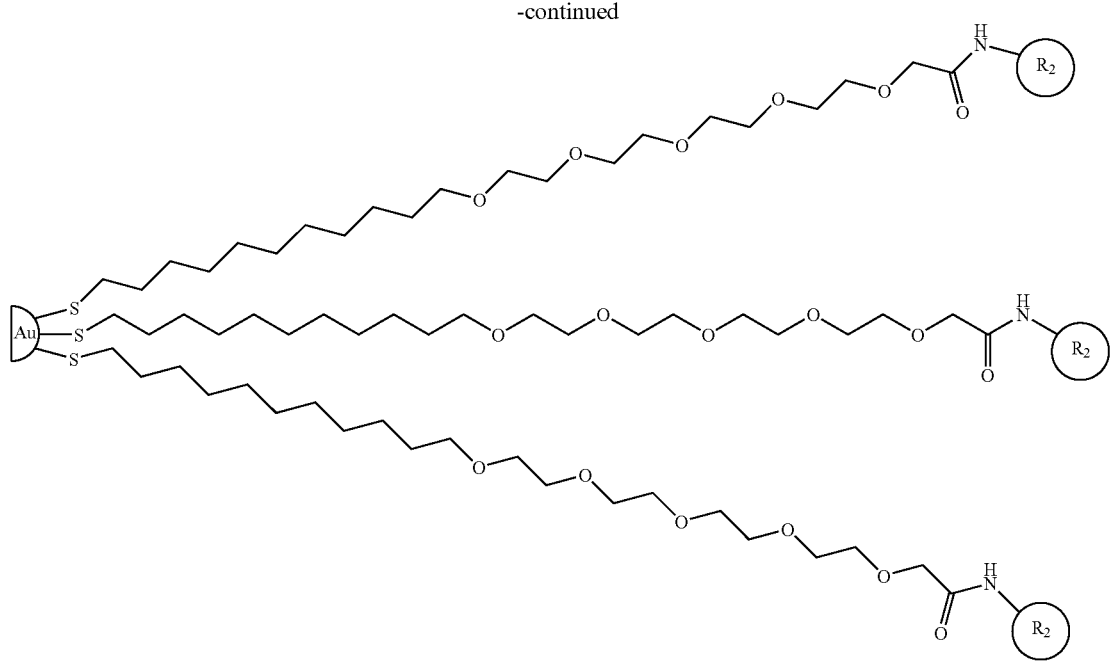

General procedure: 1-Pentanethiol coated gold nanoparticles (d=~2 nm) were prepared according to a previously reported protocol. (Brust, et al., *J. Chem. Soc. Chem. Commun.*, 1994, 801.) Place-exchange reaction of compound Ls dissolved in DCM with pentanethiol-coated gold nanoparticles (d~2 nm) was carried out for 3 days at ambient temperature. (See, Hostetler, et al., *Langmuir*, 1999, 15, 3782.) Then, DCM was evaporated under reduced pressure. The residue was dissolved in a small amount of distilled water and dialyzed (membrane MWCO=1,000) to remove excess ligands, acetic acid and the other salts present with the nanoparticles. After dialysis, the particles were lyophilized to afford a brownish solid. The nanoparticles are redispersed in deionized water (18 MΩ-cm). $^1$H NMR spectra in $D_2O$ showed substantial broadening of the proton signals and no free ligands were observed.

* * *

As demonstrated through several non-limiting embodiments, non-covalent conjugates of gold nanoparticles and a fluorescent polymer identify bacteria effectively within minutes. With this protocol, nanoparticle-bacteria interactions release an initially bound fluorescent polymer from the gold nanoparticle quencher, resulting in a "turn-on" of the polymer fluorescence. The unique fluorescence responses which are generated by the conjugates of different nanoparticles with bacterial surfaces provide an efficient means of differentiation. The efficacy of this method as shown by using 12 different bacteria, demonstrating ability to differentiate between species of bacteria as well as between differing strains of a single species, without the use of antibodies or radioactive markers.

We claim:

1. A method of detecting the presence of a pathogen analyte, the method comprising:
providing a plurality of non-covalent complexes between a plurality of nanoparticles and a fluorescent polymer,
wherein each of the plurality of nanoparticles comprises an inner metallic core and a coating layer comprising a cationic ligand,
wherein the fluorescent polymer comprises an anionic group, and
wherein fluorescence of the polymer in the non-covalent complexes is quenched;
mixing a sample to be tested for the presence of the pathogen analyte with the plurality of non-covalent complexes under a condition such that, if the pathogen analyte is presence in the sample, at least some of the fluorescent polymer is displaced by the pathogen, thereby resulting in restoration of at least some of fluorescence of the fluorescent polymer; and
measuring a fluorescence pattern of the resulting sample to determine the presence of the pathogen analyte.

2. The method of claim 1, wherein the plurality of non-covalent complexes comprise at least three non-covalent complexes between at least three different nanoparticles and a fluorescent polymer.

3. The method of claim 2, wherein the cationic ligand comprises a quaternary ammonium ion.

4. The method of claim 1, wherein the fluorescent polymer is a synthetic π-conjugated polymer.

5. The method of claim 4, wherein the synthetic π-conjugated polymer comprises a structural unit of:

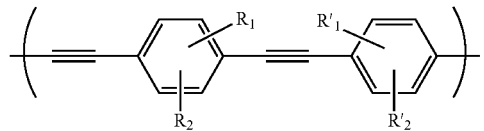

wherein $R_1$ and $R_2$ are independent selected from H, alkyl and oxa-substituted alkyl groups; $R'_1$, and $R'_2$ are independently selected from H and alkyl groups; provided that at least one of $R'_1$ and $R'_2$ comprises a charged group.

6. The method of claim 5, wherein at least one of $R'_1$, and $R'_2$ comprises a carboxylate or a sulfate anion and a counter cation.

7. The method of claim 6, wherein each of R'₁, and R'₂ is:

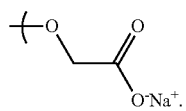

8. The method of claim 5, wherein at least one of R₁, and R₂ comprises a poly(alkylene oxide) group.

9. The method of claim 8, wherein each of R₁, and R₂ is:

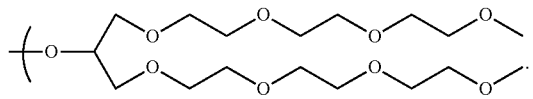

10. The method of claim 5, wherein the coating layer of each of the nanoparticles has covalently bond thereon a cationic ligand having the structure of

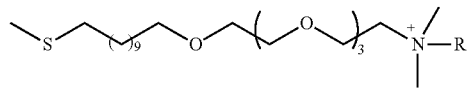

wherein R is selected from:

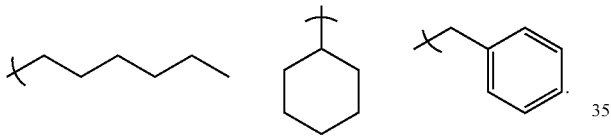

11. The method of claim 1, wherein measuring a fluorescence pattern of the resulting sample to determine the presence of the pathogen analyte comprises analyzing the fluorescent pattern by discriminate analysis.

12. A method of detecting the presence of a pathogen analyte, the method comprising:
providing a plurality of non-covalent complexes between a nanoparticle and a plurality of fluorescent polymers, wherein the nanoparticle comprises an inner metallic core and a coating layer comprising a cationic ligand, wherein each of the fluorescent polymers comprises an anionic group, and wherein fluorescence of the fluorescent polymers in the non-covalent complexes is quenched;
mixing a sample to be tested for the presence of the pathogen analyte with the plurality of non-covalent complexes under a condition such that, if the pathogen analyte is present in the sample, at least some of the fluorescent polymers are displaced by the pathogen, thereby resulting in restoration of at least some of fluorescence of the fluorescent polymers; and
measuring a fluorescence pattern of the resulting sample to determine the presence of the pathogen analyte.

13. The method of claim 12 wherein, the plurality of non-covalent complexes comprise at least three non-covalent complexes between a nanoparticle and at least three different fluorescent polymers.

14. The method of claim 13 wherein the coating layer of the nanoparticle has covalently bond thereon a cationic ligand having the structure of

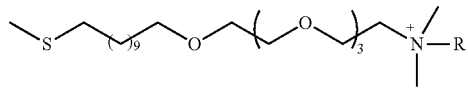

wherein R is selected from:

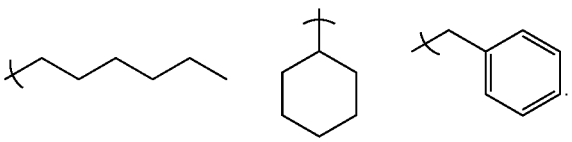

15. The method of claim 12, wherein at least one of the fluorescent polymers is a synthetic π-conjugated polymer.

16. The method of claim 15, wherein each of the π-conjugated polymers comprises a structural unit of:

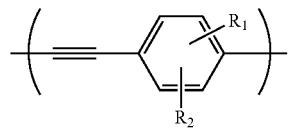

wherein R₁ and R₂ are independently selected from H, alkyl and oxa-substituted alkyl groups; provided that at least one of R₁ and R₂ comprises a charged group.

17. The method of claim 16, wherein at least one of R₁, and R₂ comprises a carboxylate or a sulfate anion and a counter cation.

18. The method of claim 17, wherein each of R₁, and R₂ is:

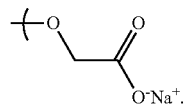

19. The method of claim 12, wherein at least one of the fluorescent polymers is a natural fluorescent protein.

20. The method of claim 19, wherein the natural fluorescent polymer comprises a green fluorescent protein.

21. The method of claim 12, wherein measuring a fluorescence pattern of the resulting sample comprises measuring a fluorescent pattern for each of the fluorescent polymers at the same wavelength.

* * * * *